(12) United States Patent
Serruto et al.

(10) Patent No.: US 8,334,114 B2
(45) Date of Patent: Dec. 18, 2012

(54) LACTOFERRIN CLEAVAGE OF NEISSERIAL PROTEINS

(75) Inventors: Davide Serruto, Siena (IT); Maria Aricò, Siena (IT)

(73) Assignee: Novartis AG, Basel (CH)

( * ) Notice: Subject to any disclaimer, the term of this patent is extended or adjusted under 35 U.S.C. 154(b) by 1192 days.

(21) Appl. No.: 11/587,191

(22) PCT Filed: Apr. 28, 2005

(86) PCT No.: PCT/IB2005/001446
§ 371 (c)(1),
(2), (4) Date: Nov. 13, 2007

(87) PCT Pub. No.: WO2005/106009
PCT Pub. Date: Nov. 10, 2005

(65) Prior Publication Data
US 2008/0193971 A1 Aug. 14, 2008

(30) Foreign Application Priority Data
Apr. 30, 2004 (GB) .................................. 0409748.1

(51) Int. Cl.
*C12P 21/06* (2006.01)
(52) U.S. Cl. .................................................... 435/68.1
(58) Field of Classification Search .................. None
See application file for complete search history.

(56) References Cited

FOREIGN PATENT DOCUMENTS

| WO | WO 9909176 A1 * | 2/1999 |
|---|---|---|
| WO | WO-99/52545 | 10/1999 |
| WO | WO 9952545 A1 * | 10/1999 |
| WO | WO-00/66741 | 11/2000 |
| WO | WO-01/64922 | 9/2001 |
| WO | WO-01/81581 A2 | 11/2001 |

OTHER PUBLICATIONS

Ng et al. (Oct. 2000). "Genome sequence of *Halobacterium* species NRC-1," Proceedings of the National Academy of Sciences USA 97(22):12176-12181.
International Search Report mailed Nov. 24, 2005, for PCT Application No. PCT/IB2005/001446 filed Apr. 28, 2005, 1 page.

* cited by examiner

*Primary Examiner* — Brian J Gangle
(74) *Attorney, Agent, or Firm* — Amy Hessler; Otis Littlefield

(57) ABSTRACT

Meningococcal antigens are cleaved by human lactoferrin. The invention is based on the identification of the cleavage products of this reaction, and provides a method for cleaving a neisserial polypeptide, comprising the step of mixing the polypeptide with a lactoferrin enzyme. The invention also provides polypeptides obtainable by this process (i.e. the cleavage products of the lactoferrin digestion). Proteins of particular interest are meningococcal proteins 287 and App.

4 Claims, 3 Drawing Sheets

LACTOFERRIN CLEAVAGE OF NEISSERIAL PROTEINS

RELATED APPLICATIONS

This application is the U.S. National Phase of International Application No. PCT/IB2005/001446, filed Apr. 28, 2005 and published in English, which claims priority to Great Britain Application No. 0409748.1, filed Apr. 30, 2004. The teachings of the above applications are incorporated in their entirety by reference.

TECHNICAL FIELD

This invention is in the field of proteolysis. In particular, it relates to the proteolytic cleavage of antigens of *Neisseria meningitidis* (meningococcus).

BACKGROUND ART

*N. meningitidis* is a non-motile, Gram-negative human pathogen that colonises the pharynx and causes meningitis (and, occasionally, septicaemia in the absence of meningitis). It causes both endemic and epidemic disease. Following the introduction of the conjugate vaccine against *Haemophilus influenzae*, *N. meningitidis* is the major cause of bacterial meningitis in the USA.

Based on the organism's capsular polysaccharide, various serogroups of *N. meningitidis* have been identified, including A, B, C, H, I, K, L, 29E, W135, X, Y & Z. Serogroup A (MenA) is the pathogen most often implicated in epidemic disease in sub-Saharan Africa. Serogroups B and C (MenB & MenC) are responsible for the vast majority of cases in the United States and in most developed countries. Serogroups W135 and Y are responsible for the rest of the cases in the USA and developed countries. Although the capsular polysaccharide is an effective protective immunogen for some serogroups, this approach is unsuitable for immunising against serogroup B.

For serogroup B, a vaccine has proved elusive. Vaccines based on outer-membrane vesicles have been tested, but protection is typically restricted to the strain that was used to make the vaccine (homologous protection). Research and development on serogroup B vaccines continues [1], with a focus on recombinant and subunit vaccines.

Genome sequences for meningococcal serogroups A [2] and B [3,4] have been reported, and the serogroup B sequence has been studied to identify vaccine antigens [e.g. refs. 5 to 10]. Candidate antigens have been manipulated to improve heterologous expression [refs. 11 to 13].

These antigens have been characterised at the level of primary sequence, and many have also been studied for post-translational processing e.g. NarE [14], NadA [15], App [16], GNA1870 [17], etc. However, it is not known how the proteins behave after administration to patients.

DISCLOSURE OF THE INVENTION

Surprisingly, the inventors have found that meningococcal antigens are cleaved by human lactoferrin. The invention is based on the identification of the cleavage products of this reaction.

Thus the invention provides a method for cleaving a neisserial polypeptide, comprising the step of mixing the polypeptide with a lactoferrin enzyme. The invention also provides polypeptides obtainable by this process (i.e. the cleavage products of the lactoferrin digestion).

*Neisseria* are known to bind to lactoferrin and to display lactoferrin receptors [MenB genes NMB1540 & NMB1541; refs. 18-24], but lactoferrin-mediated cleavage of neisserial proteins has not been reported. Cleavage of *H. influenzae* proteins by lactoferrin has been reported [25,26], but this bacterium is not closely related to *Neisseria* and there is no reason to expect that a similar activity would be seen with *Neisseria*.

The Neisserial Polypeptide

Genome sequences for serogroups A [2] and B [3,4] of meningococcus have been published, and a genome sequence for *N. gonorrhoeae* (gonococcus) strain FA 1090 is available on-line [27,28].

The neisserial polypeptide cleaved by lactoferrin according to the invention can be any of the polypeptide sequences encoded and/or expressed by a *Neisseria*, including *N. meningitidis*, *N. gonorrhoeae*, *N. lactamica*, *N. polysaccharea*, *N. subflava*, *N. sicca* and *N. cinerea*. The polypeptide is preferably from *N. meningitidis* or *N. gonorrhoeae*.

Preferred *N. meningitidis* polypeptides are those known as 'NadA', '936', '953', '287', 'App', 'TonBR' and 'NarE'. Particularly preferred are '287' and 'App'.

App Protein

'App' protein (Adhesion and penetration protein) from serogroup B meningococcus is disclosed in reference 5 (SEQ IDs 647-654) as 'ORF1', as NMB1985 in reference 3 (see also GenBank accession number GI:7227246), and as 'BASB006' in ref. 29. The corresponding protein in serogroup A [2] has GenBank accession number 7379205. App is a serine protease.

When used according to the present invention, App protein may take various forms. Preferred forms of App are truncation or deletion variants, such as those disclosed in reference 30, or the substitution mutants also disclosed in reference 30 (substitutions at Ser-267, Asp-158 and His-115).

Preferred App sequences have 50% or more identity (e.g. 60%, 70%, 80%, 90%, 95%, 99% or more) to SEQ ID NO: 1. This includes App variants (e.g. allelic variants, homologs, orthologs, paralogs, mutants, etc.). Other preferred App sequences comprise at least n consecutive amino acids from SEQ ID NO: 1, wherein n is 7 or more (e.g. 8, 10, 12, 14, 16, 18, 20, 25, 30, 35, 40, 50, 60, 70, 80, 90, 100, 150, 200, 250 or more). Preferred fragments comprise an epitope from App. Other preferred fragments lack one or more amino acids (e.g. 1, 2, 3, 4, 5, 6, 7, 8, 9, 10, 15, 20, 25 or more) from either or both of the C-terminus and/or the N-terminus of SEQ ID NO: 1.

App has Arg-rich regions (see residues 933-941 (SEQ ID NO: 22) and 1150-1156 (SEQ ID NO: 23) of SEQ ID NO: 1) that are highly conserved between different strains, and lactoferrin-catalysed cleavage occurs within one or both of these regions.

287 Protein

'287' protein from serogroup B is disclosed in reference 7 (SEQ IDs 3103 & 3104), as 'NMB2132' in reference 3, and as 'GNA2132' in reference 10 (see also GenBank accession number GI:7227388). The corresponding protein in serogroup A [2] has GenBank accession number 7379057.

When used according to the present invention, 287 protein may take various forms. Preferred forms of 287 are truncation or deletion variants, such as those disclosed in references 11 to 13. In particular, the N-terminus of 287 may be deleted up to and including its poly-glycine sequence (i.e. deletion of residues 1 to 24 for strain MC58), which is sometimes distinguished herein by the use of a 'ΔG' prefix. This deletion can enhance expression.

Preferred 287 sequences have 50% or more identity (e.g. 60%, 70%, 80%, 90%, 95%, 99% or more) to SEQ ID NO: 2. This includes 287 variants (e.g. allelic variants, homologs, orthologs, paralogs, mutants, etc.). Allelic forms of 287 can be seen in FIGS. 5 and 15 of reference 9, and in example 13 and FIG. 21 of reference 7 (SEQ IDs 3179 to 3184). Other preferred 287 sequences comprise at least n consecutive amino acids from SEQ ID NO: 2, wherein n is 7 or more (e.g. 8, 10, 12, 14, 16, 18, 20, 25, 30, 35, 40, 50, 60, 70, 80, 90, 100, 150, 200, 250 or more). Preferred fragments comprise an epitope from 287. Other preferred fragments lack one or more amino acids (e.g. 1, 2, 3, 4, 5, 6, 7, 8, 9, 10, 15, 20, 25 or more) from either or both of the C-terminus and/or the N-terminus of SEQ ID NO: 2.

Protein 287 has an Arg-rich region (see residues 237-245 (SEQ ID NO: 21) of SEQ ID NO: 2) which is highly conserved across strains. The site of lactoferrin-mediated cleavage is within this region.

NadA Protein

'NadA' (Neisserial adhesin A) from serogroup B of *N. meningitidis* is disclosed as protein '961' in reference 7 (SEQ IDs 2943 & 2944) and as 'NMB1994' in reference 3 (see also GenBank accession numbers: 11352904 & 7227256). A detailed description of the protein can be found in reference 15. There is no corresponding protein in serogroup A [2,15].

When used according to the present invention, NadA may take various forms. Preferred forms of NadA are truncation or deletion variants, such as those disclosed in references 11 to 13. In particular, NadA without its C-terminal membrane anchor is preferred (e.g. deletion of residues 351-405 for strain 2996), which is sometimes distinguished herein by the use of a 'C' superscript e.g. NadA$^{(C)}$. Expression of NadA without its membrane anchor domain in *E. coli* results in secretion of the protein into the culture supernatant with concomitant removal of its 23mer leader peptide (e.g. to leave a 327mer for strain 2996). Polypeptides without their leader peptides are sometimes distinguished herein by the use of a 'NL' superscript e.g. NadA$^{(NL)}$ or NadA$^{(C)(NL)}$.

Preferred NadA sequences have 50% or more identity (e.g. 60%, 70%, 80%, 90%, 95%, 99% or more) to SEQ ID NO: 3. This includes NadA variants (e.g. allelic variants, homologs, orthologs, paralogs, mutants, etc.). Allelic forms of NadA are shown in FIG. 9 of reference 30. Other preferred NadA sequences comprise at least n consecutive amino acids from SEQ ID NO: 3, wherein n is 7 or more (e.g. 8, 10, 12, 14, 16, 18, 20, 25, 30, 35, 40, 50, 60, 70, 80, 90, 100, 150, 200, 250 or more). Preferred fragments comprise an epitope from NadA. Other preferred fragments lack one or more amino acids (e.g. 1, 2, 3, 4, 5, 6, 7, 8, 9, 10, 15, 20, 25 or more) from either or both of the C-terminus and/or the N-terminus of SEQ ID NO: 3 (e.g. NadA$^{(C)}$, NadA$^{(NL)}$, NadA$^{(C)(NL)}$). Where N-terminus residues are deleted, it is preferred that the deletion should not remove the ability of NadA to adhere to human epithelial cells.

936 Protein

'936' protein from serogroup B is disclosed in reference 7 (SEQ IDs 2883 & 2884) and as 'NMB2091' in reference 3 (see also GenBank accession number GI:7227353). The corresponding gene in serogroup A [2] has GenBank accession number 7379093.

When used according to the present invention, 936 protein may take various forms. Preferred forms of 936 are truncation or deletion variants, such as those disclosed in references 11 to 13. In particular, the N-terminus leader peptide of 936 may be deleted (i.e. deletion of residues 1 to 23 for strain MC58 [SEQ ID 4]) to give 930$^{(NL)}$.

Preferred 936 sequences have 50% or more identity (e.g. 60%, 70%, 80%, 90%, 95%, 99% or more) to SEQ ID NO: 4. This includes variants (e.g. allelic variants, homologs, orthologs, paralogs, mutants etc). Other preferred 936 sequences comprise at least n consecutive amino acids from SEQ ID NO: 4, wherein n is 7 or more (e.g. 8, 10, 12, 14, 16, 18, 20, 25, 30, 35, 40, 50, 60, 70, 80, 90, 100, 150, 200, 250 or more). Preferred fragments comprise an epitope from 936. Other preferred fragments lack one or more amino acids (e.g. 1, 2, 3, 4, 5, 6, 7, 8, 9, 10, 15, 20, 25 or more) from either or both of the C-terminus and/or the N-terminus of SEQ ID NO: 4.

953 Protein

'953' protein from serogroup B is disclosed in reference 7 (SEQ IDs 2917 & 2918) and as 'NMB1030' in reference 3 (see also GenBank accession number GI:7226269). The corresponding protein in serogroup A [2] has GenBank accession number 7380108.

When used according to the present invention, 953 protein may take various forms. Preferred forms of 953 are truncation or deletion variants, such as those disclosed in references 11 to 13. In particular, the N-terminus leader peptide of 953 may be deleted (i.e. deletion of residues 1 to 19 for strain MC58 [SEQ ID 5]) to give 953$^{(NL)}$.

Preferred 953 sequences have 50% or more identity (e.g. 60%, 70%, 80%, 90%, 95%, 99% or more) to SEQ ID NO: 5. This includes 953 variants (e.g. allelic variants, homologs, orthologs, paralogs, mutants, etc.). Allelic forms of 953 can be seen in FIG. 19 of reference 9. Other preferred 953 sequences comprise at least n consecutive amino acids from SEQ ID NO: 5, wherein n is 7 or more (e.g. 8, 10, 12, 14, 16, 18, 20, 25, 30, 35, 40, 50, 60, 70, 80, 90, 100, 150, 200, 250 or more). Preferred fragments comprise an epitope from 953. Other preferred fragments lack one or more amino acids (e.g. 1, 2, 3, 4, 5, 6, 7, 8, 9, 10, 15, 20, 25 or more) from either or both of the C-terminus and/or the N-terminus of SEQ ID NO: 5.

'TonBR'

'TonBR' protein from serogroup B meningococcus is disclosed as 'NMB1882' in reference 3 (see also GenBank accession number GI:7227141). The corresponding protein in serogroup A [2] has GenBank accession number 7379311 [2]. TonBR is the TonB-dependent receptor (or ferric siderophore receptor).

Preferred TonBR sequences have 50% or more identity (e.g. 60%, 70%, 80%, 90%, 95%, 99% or more) to SEQ ID NO: 11. This includes TonBR variants (e.g. allelic variants, homologs, orthologs, paralogs, mutants, etc.). Other preferred TonBR sequences comprise at least n consecutive amino acids from SEQ ID NO: 11, wherein n is 7 or more (e.g. 8, 10, 12, 14, 16, 18, 20, 25, 30, 35, 40, 50, 60, 70, 80, 90, 100, 150, 200, 250 or more). Preferred fragments comprise an epitope from TonBR. Other preferred fragments lack one or more amino acids (e.g. 1, 2, 3, 4, 5, 6, 7, 8, 9, 10, 15, 20, 25 or more) from either or both of the C-terminus and/or the N-terminus of SEQ ID NO: 11.

NarE Protein

'NarE' protein from serogroup B meningococcus is disclosed as NMB1343 in reference 3 (see also GenBank accession number GI:7226587). There is no corresponding protein in serogroup A [2]. NarE is an ADP ribosyltransferase [16].

Preferred NarE sequences have 50% or more identity (e.g. 60%, 70%, 80%, 90%, 95%, 99% or more) to SEQ ID NO: 6. This includes NarE variants (e.g. allelic variants, homologs, orthologs, paralogs, mutants, etc.). Other preferred NarE sequences comprise at least n consecutive amino acids from SEQ ID NO: 6, wherein n is 7 or more (e.g. 8, 10, 12, 14, 16, 18, 20, 25, 30, 35, 40, 50, 60, 70, 80, 90, 100, 150, 200, 250 or more). Preferred fragments comprise an epitope from NarE. Other preferred fragments lack one or more amino acids (e.g. 1, 2, 3, 4, 5, 6, 7, 8, 9, 10, 15, 20, 25 or more) from either or both of the C-terminus and/or the N-terminus of SEQ ID NO: 6. Polymorphic forms of NarE are shown in FIG. 2 of ref. 13.

Other Meningococcal Proteins

Other proteins which may be cleaved by lactoferrin according to the invention include those comprising one of the following amino acid sequences: SEQ ID NO: 650 from ref. 5; SEQ ID NO: 878 from ref. 5; SEQ ID NO: 884 from ref. 5; SEQ ID NO: 4 from ref. 6; SEQ ID NO: 598 from ref. 7; SEQ ID NO: 818 from ref. 7; SEQ ID NO: 864 from ref. 7; SEQ ID NO: 866 from ref. 7; SEQ ID NO: 1196 from ref. 7; SEQ ID NO: 1272 from ref. 7; SEQ ID NO: 1274 from ref. 7; SEQ ID NO: 1640 from ref. 7; SEQ ID NO: 1788 from ref. 7; SEQ ID NO: 2288 from ref. 7; SEQ ID NO: 2466 from ref. 7; SEQ ID NO: 2554 from ref. 7; SEQ ID NO: 2576 from ref. 7; SEQ ID NO: 2606 from ref. 7; SEQ ID NO: 2608 from ref. 7; SEQ ID NO: 2616 from ref. 7; SEQ ID NO: 2668 from ref. 7; SEQ ID NO: 2780 from ref. 7; SEQ ID NO: 2932 from ref. 7; SEQ ID NO: 2958 from ref. 7; SEQ ID NO: 2970 from ref. 7; SEQ ID NO: 2988 from ref. 7, or a polypeptide comprising an amino acid sequence which: (a) has 50% or more identity (e.g. 60%, 70%, 80%, 90%, 95%, 99% or more) to said sequences; and/or (b) comprises a fragment of at least n consecutive amino acids from said sequences, wherein n is 7 or more (e.g. 8, 10, 12, 14, 16, 18, 20, 25, 30, 35, 40, 50, 60, 70, 80, 90, 100, 150, 200, 250 or more).

The Lactoferrin

Lactoferrin is a $Fe^{3+}$-binding glycoprotein, first recognized in milk and then in other human epithelial secretions and barrier fluids. Many different functions have been attributed to LF, including protection from iron-induced lipid peroxidation, immunomodulation and cell growth regulation, DNA binding, and transcriptional activation. Its physiological role is still unclear, but it has been suggested to be responsible for primary defense against microbial and viral infection. Different subfractions of purified human milk LF possess five different enzyme activities: DNase, RNase, ATPase, phosphatase, and malto-oligosaccharide hydrolysis [31]. Lactoferrin is the predominant source of these activities in human milk. Some of its catalytically active sub-fractions are cytotoxic and induce apoptosis. The enzyme can be purified from milk or expressed recombinantly. Purified lactoferrin can be obtained form various commercial suppliers.

The lactoferrin used in the method of the invention is preferably a human lactoferrin. As well as cleaving neisserial polypeptides, this enzyme has been found to cleave *H. influenzae* surface proteins at Arg-rich regions [32].

Cleavage Products

The invention also provides the cleavage products of the lactoferrin-mediated proteolysis of the invention. These fragments can be prepared by lactoferrin proteolysis, of course, or can be prepared by other means in the "already-cleaved" form. Their preparation may or may not involve proteolytic cleavage, depending on the method chosen. They may be prepared by purification from cell culture, recombinant expression, chemical synthesis (at least in part), etc. The cleavage products can take various forms (e.g. native, fusions, non-glycosylated, lipidated, etc.). They are preferably prepared in substantially pure form (i.e. substantially free from other *N. meningitidis* or host cell proteins).

A preferred cleavage product comprises an amino acid sequence of formula -A1-B1-C1-, where: A1 is an optional arginine residue; B1 is a sequence with 50% or more (e.g. 60%, 70%, 80%, 90% or 100%) sequence identity to SEQ ID NO: 7; and C1 is any amino acid sequence. Sequence C1 preferably has 50% or more (e.g. 60%, 70%, 80%, 90%, 95%, 96%, 97%, 98%, 99% or 100%) sequence identity to SEQ ID NO: 8. The -A1-B1-C1- sequence may be at the N-terminus of a polypeptide, at the C-terminus, or may have sequences both to its C- and N-termini.

Another cleavage product comprises an amino acid sequence of formula -A2-B2-, where: B2 is an optional arginine residue; and A2 is a sequence with 50% or more (e.g. 60%, 70%, 80%, 90%, 95%, 96%, 97%, 98%, 99% or 100%) sequence identity to SEQ ID NO: 9 and/or SEQ ID NO: 10. The -A2-B2- sequence may be at the N-terminus of a polypeptide, at the C-terminus, or may have sequences both to its C- and N-termini.

Where -B1- is SEQ ID NO: 7 and -C1- is SEQ ID NO: 8, -A1-B1-C1- is a proteolytic fragment of meningococcal protein 287. In this case, the optional -A1- moiety is absent in 70% of cleavages. Where -A2- is SEQ ID NO: 9, -A2-B2- is a proteolytic fragment of meningococcal protein 287. In this case, the optional -B2- moiety is absent in 30% of cleavages. Thus the sequence -A2-B2-A1-B1-C1- is protein '287' (SEQ ID NO: 2), where -B2-A1- is a single Arg residue. Where -A2- is SEQ ID NO: 10, -A2-B2-A1-B1-C1- is 'ΔG287'.

Another preferred cleavage product comprises an amino acid sequence of formula -A3-B3-C3-, where: A3 is an optional arginine residue; B3 is a sequence with 50% or more (e.g. 60%, 70%, 80%, 90% or 100%) sequence identity to SEQ ID NO: 12; and C3 is any amino acid sequence. Sequence C3 preferably has 50% or more (e.g. 60%, 70%, 80%, 90%, 95%, 96%, 97%, 98%, 99% or 100%) sequence identity to SEQ ID NO: 13. The -A3-B3-C3- sequence may be at the N-terminus of a polypeptide, at the C-terminus, or may have sequences both to its C- and N-termini.

Another preferred cleavage product comprises an amino acid sequence of formula -A4-B4-C4-, where: A4 is an optional arginine residue; B4 is a sequence with 50% or more (e.g. 60%, 70%, 80%, 90% or 100%) sequence identity to SEQ ID NO: 14; and C4 is any amino acid sequence. Sequence C4 preferably has 50% or more (e.g. 60%, 70%, 80%, 90%, 95%, 96%, 97%, 98%, 99% or 100%) sequence identity to SEQ ID NO: 15. The -A4-B4-C4- sequence may be at the N-terminus of a polypeptide, at the C-terminus, or may have sequences both to its C- and N-termini.

Another cleavage product comprises an amino acid sequence of formula -A5-B5-, where: B5 is an optional arginine residue; and A5 is a sequence with 50% or more (e.g. 60%, 70%, 80%, 90%, 95%, 96%, 97%, 98%, 99% or 100%) sequence identity to SEQ ID NO: 16. The -A5-B5- sequence may be at the N-terminus of a polypeptide, at the C-terminus, or may have sequences both to its C- and N-termini.

Another cleavage product comprises an amino acid sequence of formula -A6-B6-, where: B6 is an optional arginine residue; and A6 is a sequence with 50% or more (e.g. 60%, 70%, 80%, 90%, 95%, 96%, 97%, 98%, 99% or 100%) sequence identity to SEQ ID NO: 17. The -A6-B6- sequence may be at the N-terminus of a polypeptide, at the C-terminus, or may have sequences both to its C- and N-termini.

These polypeptides are cleavage products of App. SEQ ID NO: 1 can be made up of -A5-B5-A3-B3-C3-, where -B5-A3- is a single Arg residue. Alternatively, it can be made up of -A6-B6-A4-B4-C4-, where -B6-A4- is a single Arg residue.

Each of -A2-, -C1-, -C3-, -C4-, -A5- and -A6- preferably consists of at least 10 amino acids (e.g. at least 12, 14, 16, 18, 20, 25, 30, 40, 50, 60, 70, 80, 90, 100, 150, 200, 250, 300, 400, 500 or more).

Preferably the polypeptide comprising sequence -A1-B1-C1- does not include the amino acid sequence SEQ ID NO: 18 and/or SEQ ID NO: 21. Preferably the polypeptide comprising sequence -A2-B2- does not include the amino acid sequence SEQ ID NO: 7. Preferably the polypeptide comprising sequence -A3-B3-C3- does not include the amino acid sequence SEQ ID NO: 19 and/or SEQ ID NO: 22. Preferably the polypeptide comprising sequence -A4-B4-C4- does not include the amino acid sequence SEQ ID NO: 20 and/or SEQ ID NO: 23. Preferably the polypeptide comprising sequence -A5-B5- does not include the amino acid sequence SEQ ID NO: 12. Preferably the polypeptide comprising sequence -A6-B6- does not include amino acid sequence SEQ ID NO: 14.

The invention also provides nucleic acid encoding cleavage products. Furthermore, the invention provides nucleic acid which can hybridise to this nucleic acid, preferably under "high stringency" conditions (e.g. 65° C. in a 0.1xSSC, 0.5% SDS solution).

Nucleic acid according to the invention can be prepared in many ways (e.g. by chemical synthesis (at least in part), from genomic or cDNA libraries, from the organism itself, etc.) and can take various forms (e.g. single stranded, double stranded, vectors, probes, etc.). They are preferably prepared in substantially pure form (i.e. substantially free from other $N.$ $meningitidis$ or host cell nucleic acids).

The term "nucleic acid" includes DNA and RNA, and also their analogues, such as those containing modified backbones (e.g. phosphorothioates, etc.), and also peptide nucleic acids (PNA) etc. The invention includes nucleic acid comprising sequences complementary to those described above (e.g. for antisense or probing purposes).

The invention also provides a process for producing a polypeptide of the invention, comprising the step of culturing a host cell transformed with nucleic acid of the invention under conditions which induce polypeptide expression.

The invention provides a process for producing a polypeptide of the invention, comprising the step of synthesising at least part of the polypeptide by chemical means.

The invention provides a process for producing nucleic acid of the invention, comprising the step of amplifying nucleic acid using a primer-based amplification method (e.g. PCR).

The invention provides a process for producing nucleic acid of the invention, comprising the step of synthesising at least part of the nucleic acid by chemical means.

Strains

Meningococcal proteins cleaved by lactoferrin can be taken from any strain, and the use of a particular strain for exemplification herein should not be seen as limiting.

Preferred proteins of the invention comprise an amino acid sequence found in $N.$ $meningitidis$ serogroup B. Within serogroup B, preferred strains are 2996, MC58, 95N477, and 394/98. Strain 394/98 is sometimes referred to herein as 'NZ', as it is a New Zealand strain.

Protein 287 is preferably from strain 2996 or, more preferably, from strain 394/98.

Proteins 936, 953 and NadA are preferably from strain 2996.

Strains may be indicated as a subscript e.g. $NadA_{MC58}$ is protein NadA from strain MC58. Unless otherwise stated, proteins mentioned herein (e.g. with no subscript) are from $N.$ $meningitidis$ strain 2996, which can be taken as a 'reference' strain. It will be appreciated, however, that the invention is not in general limited by strain. As mentioned above, general references to a protein (e.g. '287', '919' etc.) may be taken to include that protein from any strain. This will typically have sequence identity to 2996 of 90% or more (e.g. 91%, 92%, 93%, 94%, 95%, 96%, 97%, 98%, 99% or more).

Where a composition includes a particular protein antigen (e.g. 287 or NadA), the composition can include that antigen in more than one variant form e.g. the same protein, but from more than one strain. These proteins may be included as tandem or separate proteins.

Heterologous Host

Whilst expression of the proteins of the invention may take place in $Neisseria,$ the present invention preferably utilises a heterologous host. The heterologous host may be prokaryotic (e.g. a bacterium) or eukaryotic. It is preferably $E.$ $coli,$ but other suitable hosts include $Bacillus$ $subtilis,$ $Vibrio$ $cholerae,$ $Salmonella$ $typhi,$ $Salmonella$ $typhimurium,$ $Neisseria$ $lactamica,$ $Neisseria$ $cinerea,$ $Mycobacteria$ (e.g. $M.$ $tuberculosis$), yeast, etc.

Immunogenic Compositions and Medicaments

The invention provides an immunogenic composition comprising a polypeptide of the invention. Such compositions are preferably vaccine compositions. Vaccines according to the invention may either be prophylactic (i.e. to prevent infection) or therapeutic (i.e. to treat infection), but will typically be prophylactic.

The pH of the composition is preferably between 6 and 8, preferably about 7. Stable pH may be maintained by the use of a buffer. Where a composition comprises an aluminium hydroxide salt, it is preferred to use a histidine buffer [33]. The composition may be sterile and/or pyrogen-free. Compositions of the invention may be isotonic with respect to humans.

Compositions may be presented in vials, or they may be presented in ready-filled syringes. The syringes may be supplied with or without needles. A syringe will include a single dose of the composition, whereas a vial may include a single dose or multiple doses. Injectable compositions will usually be liquid solutions or suspensions. Alternatively, they may be presented in solid form (e.g. freeze-dried) for solution or suspension in liquid vehicles prior to injection.

Compositions of the invention may be packaged in unit dose form or in multiple dose form. For multiple dose forms, vials are preferred to pre-filled syringes. Effective dosage volumes can be routinely established, but a typical human dose of the composition for injection has a volume of 0.5 ml.

Where a composition of the invention is to be prepared extemporaneously prior to use (e.g. where a component is presented in lyophilised form) and is presented as a kit, the kit may comprise two vials, or it may comprise one ready-filled syringe and one vial, with the contents of the syringe being used to reactivate the contents of the vial prior to injection.

The invention also provides a composition of the invention for use as a medicament. The medicament is preferably able to raise an immune response in a mammal (i.e. it is an immunogenic composition) and is more preferably a vaccine.

The invention also provides the use of a composition of the invention in the manufacture of a medicament for raising an immune response in a mammal. It also provides the use of a polypeptide of the invention in the manufacture of a medicament for raising an immune response in a mammal. The medicament is preferably a vaccine.

The invention also provides a method for raising an immune response in a mammal comprising the step of administering an effective amount of a composition of the invention. The immune response is preferably protective and preferably involves antibodies. The method may raise a booster response.

The mammal is preferably a human. Where the vaccine is for prophylactic use, the human is preferably a child (e.g. a toddler or infant); where the vaccine is for therapeutic use, the human is preferably an adult. A vaccine intended for children may also be administered to adults e.g. to assess safety, dosage, immunogenicity, etc.

These uses and methods are preferably for the prevention and/or treatment of a disease caused by a *Neisseria* (e.g. meningitis, septicaemia, bacteremia, gonorrhoea etc.). The prevention and/or treatment of bacterial or meningococcal meningitis is preferred.

One way of checking efficacy of therapeutic treatment involves monitoring Neisserial infection after administration of the composition of the invention. One way of checking efficacy of prophylactic treatment involves monitoring immune responses against antigens after administration of the composition. Immunogenicity of compositions of the invention can be determined by administering them to test subjects (e.g. children 12-16 months age, or animal models [34]) and then determining standard parameters including serum bactericidal antibodies (SBA) and ELISA titres (GMT) of total and high-avidity IgG. These immune responses will generally be determined around 4 weeks after administration of the composition, and compared to values determined before administration of the composition. A SBA increase of at least 4-fold or 8-fold is preferred. Where more than one dose of the composition is administered, more than one post-administration determination may be made.

Preferred compositions of the invention can confer an antibody titre in a patient that is superior to the criterion for seroprotection for each antigenic component for an acceptable percentage of human subjects. Antigens with an associated antibody titre above which a host is considered to be seroconverted against the antigen are well known, and such titres are published by organisations such as WHO. Preferably more than 80% of a statistically significant sample of subjects is seroconverted, more preferably more than 90%, still more preferably more than 93% and most preferably 96-100%.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, intranasal, ocular, aural, pulmonary or other mucosal administration. Intramuscular administration to the thigh or the upper arm is preferred. Injection may be via a needle (e.g. a hypodermic needle), but needle-free injection may alternatively be used. A typical intramuscular dose is 0.5 ml.

The invention may be used to elicit systemic and/or mucosal immunity.

Dosage treatment can be a single dose schedule or a multiple dose schedule. Multiple doses may be used in a primary immunisation schedule and/or in a booster immunisation schedule. A primary dose schedule may be followed by a booster dose schedule. Suitable timing between priming doses (e.g. between 4-16 weeks), and between priming and boosting, can be routinely determined.

Neisserial infections affect various areas of the body and so the compositions of the invention may be prepared in various forms. For example, the compositions may be prepared as injectables, either as liquid solutions or suspensions. Solid forms suitable for solution in, or suspension in, liquid vehicles prior to injection can also be prepared (e.g. a lyophilised composition). The composition may be prepared for topical administration e.g. as an ointment, cream or powder. The composition be prepared for oral administration e.g. as a tablet or capsule, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as spray, drops, gel or powder [e.g. 35 & 36].

Immunogenic compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials, and a typical quantity of each antigen per dose is between 1 µg and 20 µg e.g. about 1 µg, about 2.5 µg, about 4 µg, about 5 µg, or about 10 µg.

The composition of the invention will typically, in addition to the components mentioned above, comprise one or more 'pharmaceutically acceptable carriers', which include any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, sucrose [37], trehalose [38], lactose, and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. Sterile pyrogen-free, phosphate-buffered physiologic saline is a typical carrier. A thorough discussion of pharmaceutically acceptable excipients is available in reference 39.

Compositions of the invention may include an antimicrobial, particularly when packaged in multiple dose format.

Compositions of the invention may comprise detergent e.g. a Tween (polysorbate), such as Tween 80. Detergents are generally present at low levels e.g. <0.01%.

Compositions of the invention may include sodium salts (e.g. sodium chloride) to give tonicity. A concentration of 10±2 mg/ml NaCl is typical.

Compositions of the invention will generally include a buffer. A phosphate buffer is typical.

Compositions of the invention may comprise a sugar alcohol (e.g. mannitol) or a disaccharide (e.g. sucrose or trehalose) e.g. at around 15-30 mg/ml (e.g. 25 mg/ml), particularly if they are to be lyophilised or if they include material which has been reconstituted from lyophilised material. The pH of a composition for lyophilisation may be adjusted to around 6.1 prior to lyophilisation.

Vaccines of the invention may be administered in conjunction with other immunoregulatory agents. In particular, compositions will usually include an adjuvant. Adjuvants which may be used in compositions of the invention include, but are not limited to:

A. Mineral-containing Compositions

Mineral containing compositions suitable for use as adjuvants in the invention include mineral salts, such as aluminium salts and calcium salts. The invention includes mineral salts such as hydroxides (e.g. oxyhydroxides), phosphates (e.g. hydroxyphosphates, orthophosphates), sulphates, etc. [e.g. see chapters 8 & 9 of ref. 40], or mixtures of different mineral compounds, with the compounds taking any suitable form (e.g. gel, crystalline, amorphous, etc.), and with adsorption being preferred. The mineral containing compositions may also be formulated as a particle of metal salt [41].

Aluminium phosphates are particularly preferred, particularly in compositions which include a *H. influenzae* saccharide antigen, and a typical adjuvant is amorphous aluminium hydroxyphosphate with $PO_4$/Al molar ratio between 0.84 and 0.92, included at 0.6 mg $Al^{3+}$/ml. Adsorption with a low dose of aluminium phosphate may be used e.g. between 50 and 100 μg $Al^{3+}$ per conjugate per dose. Where there is more than one conjugate in a composition, not all conjugates need to be adsorbed.

B. Oil Emulsions

Oil emulsion compositions suitable for use as adjuvants in the invention include squalene-water emulsions, such as MF59 [Chapter 10 of ref. 40; see also ref. 42] (5% Squalene, 0.5% Tween 80, and 0.5% Span 85, formulated into submicron particles using a microfluidizer). Complete Freund's adjuvant (CFA) and incomplete Freund's adjuvant (IFA) may also be used.

C. Saponin Formulations [chapter 22 of ref. 40]

Saponin formulations may also be used as adjuvants in the invention. Saponins are a heterologous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as Stimulon™.

Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref. 43. Saponin formulations may also comprise a sterol, such as cholesterol [44].

Combinations of saponins and cholesterols can be used to form unique particles called immunostimulating complexes (ISCOMs) [chapter 23 of ref. 40]. ISCOMs typically also include a phospholipid such as phosphatidylethanolamine or phosphatidylcholine. Any known saponin can be used in ISCOMs. Preferably, the ISCOM includes one or more of QuilA, QHA & QHC. ISCOMs are further described in refs. 44-46. Optionally, the ISCOMS may be devoid of additional detergent [47].

A review of the development of saponin based adjuvants can be found in refs. 48 & 49.

D. Virosomes and Virus-like Particles

Virosomes and virus-like particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in refs. 50-55. Virosomes are discussed further in, for example, ref. 56

E. Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof.

Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in ref. 57. Such "small particles" of 3dMPL are small enough to be sterile filtered through a 0.22 μm membrane [57]. Other non-toxic LPS derivatives include monophosphoryl lipid A mimics, such as aminoalkyl glucosaminide phosphate derivatives e.g. RC-529 [58,59].

Lipid A derivatives include derivatives of lipid A from *Escherichia coli* such as OM-174. OM-174 is described for example in refs. 60 & 61.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. References 62, 63 and 64 disclose possible analog substitutions e.g. replacement of guanosine with 2'-deoxy-7-deazaguanosine. The adjuvant effect of CpG oligonucleotides is further discussed in refs. 65-70.

The CpG sequence may be directed to TLR9, such as the motif GTCGTT or TTCGTT [71]. The CpG sequence may be specific for inducing a Th1 immune response, such as a CpG-A ODN, or it may be more specific for inducing a B cell response, such a CpG-B ODN. CpG-A and CpG-B ODNs are discussed in refs. 72-74. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, refs. 71 & 75-77.

Bacterial ADP-ribosylating toxins and detoxified derivatives thereof may be used as adjuvants in the invention. Preferably, the protein is derived from *E. coli* (*E. coli* heat labile enterotoxin "LT"), cholera ("CT"), or pertussis ("PT"). The use of detoxified ADP-ribosylating toxins as mucosal adjuvants is described in ref. 78 and as parenteral adjuvants in ref. 79. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivatives thereof, particularly LT-K63 and LT-R72, as adjuvants can be found in refs. 80-87. Numerical reference for amino acid substitutions is preferably based on the alignments of the A and B subunits of ADP-ribosylating toxins set forth in ref. 88, specifically incorporated herein by reference in its entirety.

F. Human Immunomodulators

Human immunomodulators suitable for use as adjuvants in the invention include cytokines, such as interleukins (e.g. IL-1, IL-2, IL-4, IL-5, IL-6, IL-7, IL-12 [89], etc.) [90], interferons (e.g. interferon-γ), macrophage colony stimulating factor, and tumor necrosis factor.

G. Bioadhesives and Mucoadhesives

Bioadhesives and mucoadhesives may also be used as adjuvants in the invention. Suitable bioadhesives include esterified hyaluronic acid microspheres [91] or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention [92].

H. Microparticles

Microparticles may also be used as adjuvants in the invention. Microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

I. Liposomes (Chapters 13 & 14 of ref. 40)

Examples of liposome formulations suitable for use as adjuvants are described in refs. 93-95.

J. Polyoxyethylene Ether and Polyoxyethylene Ester Formulations

Adjuvants suitable for use in the invention include polyoxyethylene ethers and polyoxyethylene esters [96]. Such formulations further include polyoxyethylene sorbitan ester surfactants in combination with an octoxynol [97] as well as polyoxyethylene alkyl ethers or ester surfactants in combination with at least one additional non-ionic surfactant such as an octoxynol [98]. Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

K. Polyphosphazene (PCPP)

PCPP formulations are described, for example, in refs. 99 and 100.

L. Muramyl Peptides

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine MTP-PE).

M. Imidazoquinolone Compounds

Examples of imidazoquinolone compounds suitable for use adjuvants in the invention include Imiquamod and its homologues (e.g. "Resiquimod 3M"), described further in refs. 101 and 102.

The invention may also comprise combinations of aspects of one or more of the adjuvants identified above. For example, the following adjuvant compositions may be used in the invention: (1) a saponin and an oil-in-water emulsion [103]; (2) a saponin (e.g. QS21)+a non-toxic LPS derivative (e.g. 3dMPL) [104]; (3) a saponin (e.g. QS21)+a non-toxic LPS derivative (e.g. 3dMPL)+a cholesterol; (4) a saponin (e.g. QS21)+3dMPL+IL-12 (optionally+a sterol)[105]; (5) combinations of 3dMPL with, for example, QS21 and/or oil-in-water emulsions [106]; (6) SAF, containing 10% squalane, 0.4% Tween 80™, 5% pluronic-block polymer L121, and thr-MDP, either microfluidized into a submicron emulsion or vortexed to generate a larger particle size emulsion. (7) Ribi™ adjuvant system (RAS), (Ribi Immunochem) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); and (8) one or more mineral salts (such as an aluminum salt)+a non-toxic derivative of LPS (such as 3dMPL).

Other substances that act as immunostimulating agents are disclosed in chapter 7 of ref. 40.

The use of an aluminium hydroxide or aluminium phosphate adjuvant is particularly preferred, and antigens are generally adsorbed to these salts. Aluminium hydroxide is preferably avoided as an adjuvant if the composition includes a Hib antigen. Where an aluminium phosphate it used and desired not to adsorb an antigen to the adjuvant, this is favoured by including free phosphate ions in solution (e.g. by the use of a phosphate buffer). Prevention of adsorption can also be achieved by selecting the correct pH during antigen/adjuvant mixing, an adjuvant with an appropriate point of zero charge, and an appropriate order of mixing for different antigens in a composition [107].

Calcium phosphate is another preferred adjuvant.

Further Antigens

Compositions of the invention contain five basic meningococcal protein antigens. They may also include further antigens, although it may contain no meningococcal protein antigens other than the five basic antigens. Further antigens for inclusion may be, for example:

a saccharide antigen from *Haemophilus influenzae* B.

a saccharide antigen from *N. meningitidis* serogroup A, C, W135 and/or Y, such as the oligosaccharide disclosed in ref. 108 from serogroup C or the oligosaccharides of ref. 109.

a saccharide antigen from *Streptococcus pneumoniae* [e.g. refs. 110 to 112].

an antigen from hepatitis A virus, such as inactivated virus [e.g. 113, 114].

an antigen from hepatitis B virus, such as the surface and/or core antigens [e.g. 114, 115].

a diphtheria antigen, such as a diphtheria toxoid [e.g. chapter 3 of ref. 116] e.g. the $CRM_{197}$ mutant [e.g. 117].

a tetanus antigen, such as a tetanus toxoid [e.g. chapter 4 of ref. 116].

an antigen from *Bordetella pertussis*, such as pertussis holotoxin (PT) and filamentous haemagglutinin (FHA) from *B. pertussis*, optionally also in combination with pertactin and/or agglutinogens 2 and 3 [e.g. refs. 118 & 119]. Cellular pertussis antigen may be used.

an outer-membrane vesicle (OMV) preparation from *N. meningitidis* serogroup B, such as those disclosed in refs. 120, 121, 122 etc.

polio antigen(s) [e.g. 123, 124] such as OPV or, preferably, IPV.

The composition may comprise one or more of these further antigens. Antigens will typically be present at a concentration of at least 1 μg/ml each. In general, the concentration of any given antigen will be sufficient to elicit an immune response against that antigen. It is preferred that the protective efficacy of individual saccharide antigens is not removed by combining them, although actual immunogenicity (e.g. ELISA titres) may be reduced.

Where a diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens. Such DTP combinations can be used to reconstitute lyophilised conjugates.

Where a saccharide or carbohydrate antigen is used, it is preferably conjugated to a carrier protein in order to enhance immunogenicity. Covalent conjugation is a well known technique. Preferred carrier proteins are bacterial toxins or toxoids, such as diphtheria toxoid or tetanus toxoid. The $CRM_{197}$ diphtheria toxoid [125-127] is particularly preferred. Other suitable carrier proteins include the *N. meningitidis* outer membrane protein [128], synthetic peptides [129,130], heat shock proteins [131,132], pertussis proteins [133,134], cytokines [135], lymphokines [135], hormones [135], growth factors [135], artificial proteins comprising multiple human $CD4^+$ T cell epitopes from various pathogen-derived antigens [136], protein D from *H. influenzae* [137,138], pneumococcal surface protein PspA [139], iron-uptake proteins [140], toxin A or B from *C. difficile* [141], etc. Preferred carriers are diphtheria toxoid, tetanus toxoid, *H. influenzae* protein D, and $CRM_{197}$.

Any suitable conjugation reaction can be used, with any suitable linker where necessary. The saccharide will typically be activated or functionalised prior to conjugation. Activation may involve, for example, cyanylating reagents such as CDAP (e.g. 1-cyano-4-dimethylamino pyridinium tetrafluoroborate [142,143, etc.]). Other suitable techniques use carbodiimides, hydrazides, active esters, norborane, p-nitrobenzoic acid, N-hydroxysuccinimide, S-NHS, EDC, TSTU. Linkages via a linker group may be made using any known procedure, for example, the procedures described in references 144 and 145. One type of linkage involves reductive amination of the polysaccharide, coupling the resulting amino group with one end of an adipic acid linker group, and then coupling a protein to the other end of the adipic acid linker group [146,147]. Other linkers include B-propionamido [148], nitrophenyl-ethylamine [149], haloacyl halides [150], glycosidic linkages [151], 6-aminocaproic acid [152], ADH [153], $C_4$ to $C_{12}$ moieties [154] etc. As an alternative to using a linker, direct linkage can be used. Direct linkages to the protein may comprise oxidation of the polysaccharide followed by reductive amination with the protein, as described in, for example, references 155 and 156.

Toxic protein antigens may be detoxified where necessary (e.g. detoxification of pertussis toxin by chemical and/or genetic means [119]).

As an alternative to using protein antigens in the composition of the invention, nucleic acid encoding the antigen may be used [e.g. refs. 157 to 165]. Protein components of the compositions of the invention may thus be replaced by nucleic acid (preferably DNA e.g. in the form of a plasmid) that encodes the protein. Similarly, compositions of the invention may comprise proteins which mimic saccharide antigens e.g. mimotopes [166] or anti-idiotype antibodies. These may replace individual saccharide components, or may supplement them. As an example, the vaccine may comprise a peptide mimic of the MenC [167] or the MenA [168] capsular polysaccharide in place of the saccharide itself.

Particularly preferred compositions of the invention include one, two or three of: (a) saccharide antigens from meningococcus serogroups Y, W135, C and (optionally) A; (b) a saccharide antigen from *Haemophilus influenzae* type B; and/or (c) an antigen from *Streptococcus pneumoniae*. A composition comprising the serogroup B antigens and a Hib conjugate is particularly preferred.

General

The term "comprising" encompasses "including" as well as "consisting" e.g. a composition "comprising" X may consist exclusively of X or may include something additional e.g. X+Y.

The term "about" in relation to a numerical value x means, for example, x±10%.

The word "substantially" does not exclude "completely" e.g. a composition which is "substantially free" from Y may be completely free from Y. Where necessary, the word "substantially" may be omitted from the definition of the invention.

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of reference 169. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is taught in reference 170.

Sequences included to facilitate cloning or purification, etc., do not necessarily contribute to the invention and may be omitted or removed.

This invention does not include within its scope any of the 287 or App fragments disclosed in the prior art e.g. in the documents cited herein.

MODES FOR CARRYING OUT THE INVENTION

Protein 287

Figure 1:
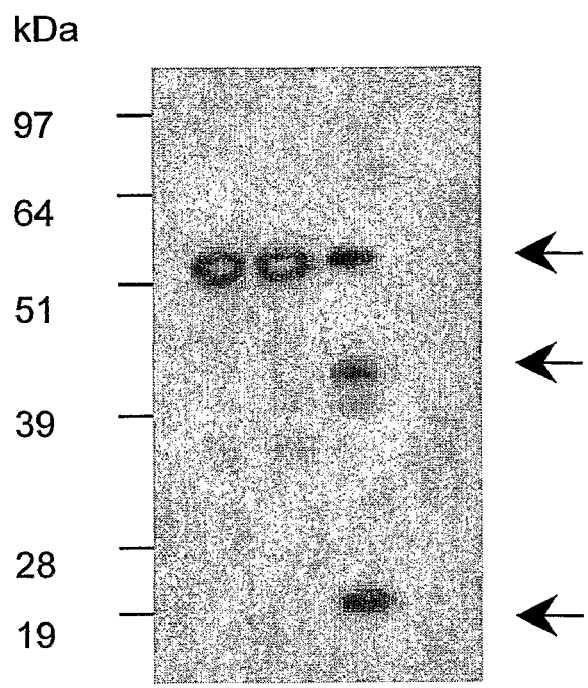
FIGS. 1 and 2 are western blots using anti-287 showing the effect of lactoferrin on (1) purified protein 287 or (2) meningococcal bacteria.

An example of a full length 287 sequence is given in SEQ ID NO: 2. 0.5 µg of 287 was mixed with 10 µg human lactoferrin in a 20 µl reaction volume. The mixture was incubated at 37° C. for 2 hours, and 10 µl of the mixture was then analysed by SDS-PAGE followed by a western blot using rabbit anti-287 (1:8000 dilution). The results are shown in FIG. 1. The lanes show: (1) 287 in Tris buffer at room temperature; (2) 287 in Tris buffer at 37° C.; (3) 287 in Tris buffer with lactoferrin at 37° C.; and (4) lactoferrin in PBS buffer at 37° C. Lane 3 shows definite cleavage of protein 287. The sizes of the fragments (~40 kDa and ~19 kDa) are consistent with cleavage at the Arg-rich region in 287.

As a further control, the inhibitor decanoyl-RVKR-chloromethylketone was included in the reaction mixture. Cleavage was inhibited in the presence of this compound.

Figure 2:
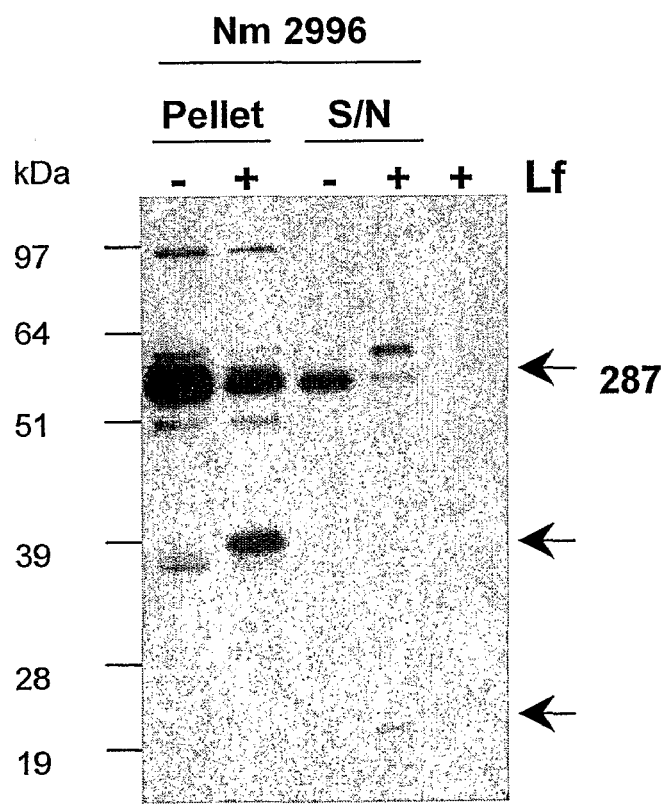

The effect of lactoferrin on meningococcal cells was also investigated. 1 ml of log phase culture (OD=0.5) of strain 2996 was washed with Tris buffered saline and then incubated with 120 μl of 1 mg/ml lactoferrin for 2 hours at 37° C. The mixture was centrifuged and the cell pellet and supernatant were analysed by SDS-PAGE as described above. Results are shown in FIG. 2. Cleavage is seen, with the ~19 kDa fragment being seen only in the supernatant. Thus the cleavage seems to release the C-terminal region of the protein into the supernatant.

The ~19 kDa fragment of cleavage was subjected to N-terminus sequences. Two different N-termini 9 mer sequences were seen: SLPAEMPLI (SEQ ID NO: 24) (~70%) and RSLPAEMPL (SEQ ID NO: 25) (~30%). These sequences are immediately downstream of the Arg-rich region in SEQ ID NO: 2 and differ only by one amino acid:

```
MFERSVIAMACIFALSACGGGGGSPDVKSADTLSKPAAPVVAEKETEVK

EDAPQAGSQGQGAPSTQGSQDMAAVSAENTGNGGAATTDKPKNEDEGPQN

DMPQNSAESANQTGNNQPADSSDSAPASNPAPANGGSNFGRVDLANGVLI

DGPSQNITLTHCKGDSCNGDNLLDEEAPSKSEFENLNESERIEKYKKDGK

SDKFTNLVATAVQANGTNKYVIIYKDKSASSSSARFRRSARSRRSLPAEM

PLIPVNQADGLIVDGEAVSLTGHSGNIFAPEGNYRYLTYGAEKLPGGSYA

LRVQGEPAKGEMLAGTAVYNGEVLHFHTENGRPYPTRGRFAAKVDFGSKS

VDGIIDSGDDLHMGTQKFKAAIDGNGFKGTWTENGGGDVSGRFYGPAGEE

VAGKYSYRPTDAEKGGFGVFAGKKEQD
```

287 protein is an effective antigen for raising bactericidal antibody responses. The effect of lactoferrin treatment on this activity was tested. After treating meningococcus strain 2996 with human lactoferrin or with PBS buffer for 2 hours at 37° C., the bactericidal assay was performed using serum obtained using uncleaved ΔG287 (adjuvanted either with alum or CFA). As a negative control, antiserum to NadA was used. As a positive control, the SEAM3 antibody was used.

Figure 3:
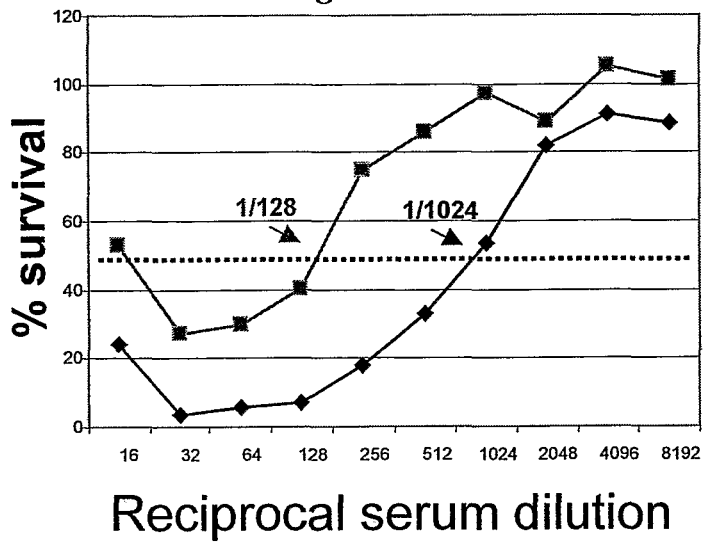
FIGS. 3 and 4 show results of serum bactericidal assays using anti-287 serum. Bacteria were either treated (■) or untreated (♦) with lactoferrin. The 287 used to generate the serum was adjuvated either with aluminum hydroxide (FIG. 3) or with complete Freund's adjuvant (FIG. 4).
Figure 4:
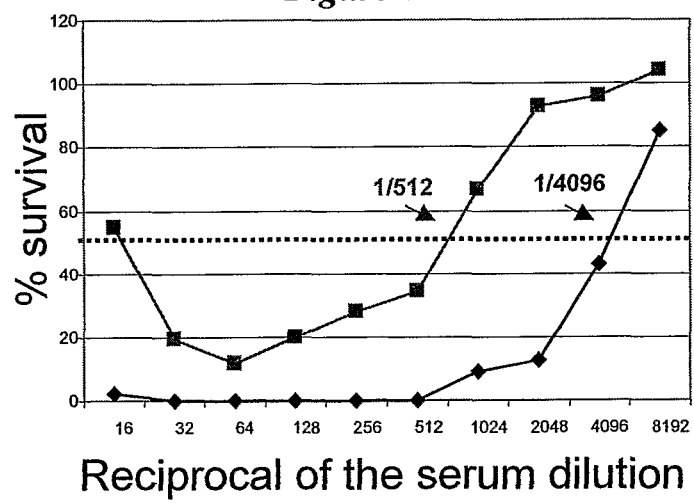
Figure 5:
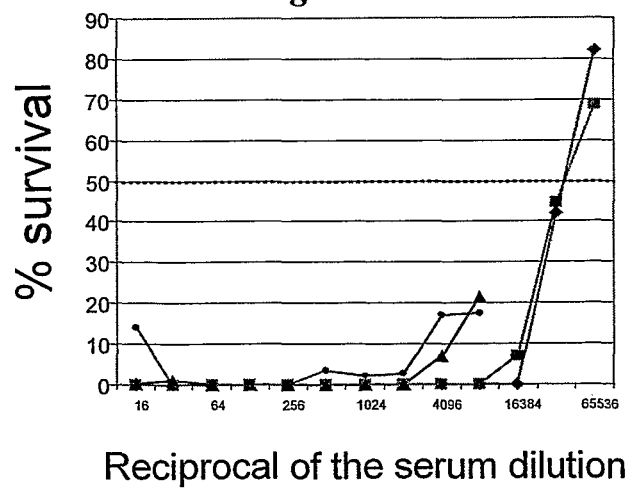
FIG. 5 shows results of serum bactericidal assays using anti-NadA serum (▲ & ●) or SEAM3 (■ & ♦). Bacteria were either treated (■ & ●) or untreated (♦ & ▲) with lactoferrin.

FIGS. 3 and 4 show that anti-287 serum is less effective against lactoferrin-treated bacteria than against the untreated bacteria. In both cases the serum was active for three further serial dilutions against the untreated bacteria. In contrast, lactoferrin treatment had no effect on the bactericidal activity of anti-NadA serum or of the SEAM3 antibody (FIG. 5).

App

Figure 6:
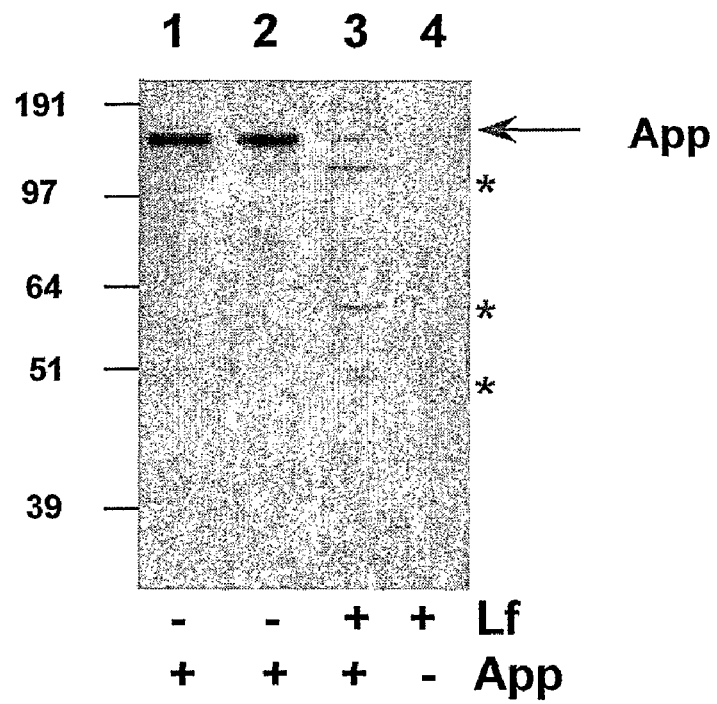
FIGS. 6 and 7 are western blots using anti-App showing the effect of lactoferrin on (6) purified App or (7) meningococcal bacteria. Asterisks show degradation products.

An example of a full length App sequence is given in SEQ ID NO: 1. 0.5 μg of recombinant App was incubated at 37° C. for 2 hours with 10 μg human lactoferrin in a 20 μl reaction volume. Western blot analysis using anti-App (1:1000 dilution) showed that the App antigen was cleaved in different fragments (FIG. 6). In FIG. 6, the lanes are: (1) App+PBS buffer at 25° C.; (2) App+PBS buffer at 37° C.; (3) App+Lf at 37° C.; (4) Lf+PBS.

Figure 7:
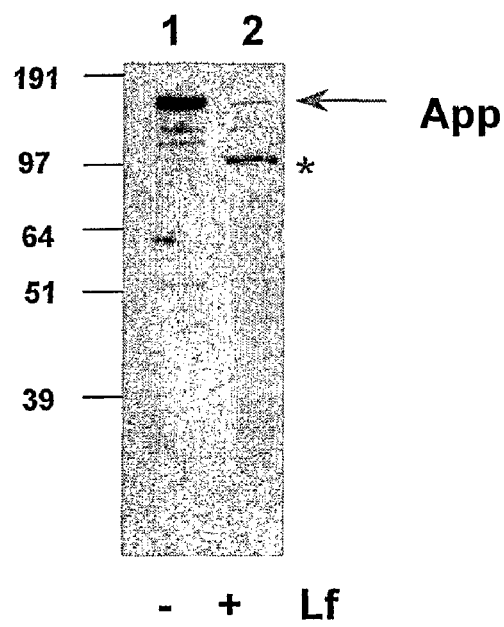

In additional experiments, N. meningitidis strain MC58 bacteria were resuspended in human lactoferrin and incubated for 2 hours at 37° C. After incubation, whole cells lysates were examined by western immunoblotting using an anti-App antiserum. As shown in FIG. 7, treatment with lactoferrin degraded the protein generating a fragment of ~97 kDa in the bacterial cell pellet.

Figure 8:
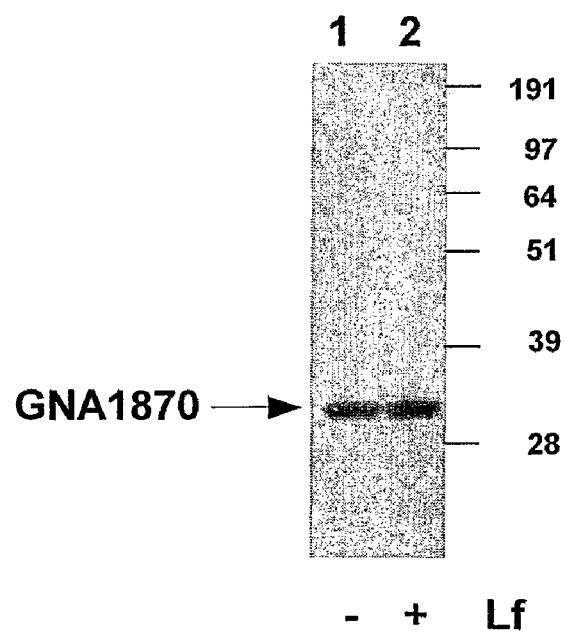
FIG. 8 is a western blot using anti-GNA1870 showing the effect of lactoferrin on meningococci.

To address the specificity of the interaction between Lf and meningococcal surface proteins, the effect of Lf treatment on GNA1870 [17] surface-exposed lipoprotein was tested. As shown in FIG. 8, lactoferrin treatment under conditions which degrade App had no effect on GNA1870

It will be understood that the invention has been described by way of example only and modifications may be made whilst remaining within the scope and spirit of the invention.
REFERENCES (The Contents of Which are Hereby Incorporated by Reference)

[1] Bethell & Pollard (2003) *Expert Rev Vaccines* 1:75-84.
[2] Parkhill et al. (2000) *Nature* 404:502-506.
[3] Tettelin et al. (2000) *Science* 287:1809-1815.
[4] WO00/66791.
[5] WO99/24578.
[6] WO99/36544.
[7] WO99/57280.
[8] WO00/22430.
[9] WO00/66741.
[10] Pizza et al. (2000) *Science* 287:1816-1820.
[11] WO01/64920.
[12] WO01/64922.
[13] WO03/020756.
[14] Masignani et al. (2003) *Mol Microbiol* 50:1055-67.
[15] Comanducci et al. (2002) *J. Exp. Med.* 195:1445-1454.
[16] Serruto et al. (2003) *Mol Microbiol* 48:323-34.
[17] Masignani et al. (2003) *J Exp Med* 197:789-799.
[18] WO99/09176.
[19] Anderson et al. (2003) *Mol Microbial* 28:1325-1337.
[20] Desai et al. (2000) *J Bacteriol* 182:5586-5591.
[21] Prinz et al. (1999) *J Bacteriol* 181:4417-9.
[22] Pettersson et al. (1999) *Gene* 231:105-10.
[23] Biswas et al. (1999) *Infect Immun* 67:455-459.
[24] Lewis et al. (1998) *Infect Immun* 66:3017-23.
[25] Qiu et al. (1998) *PNAS USA* 95:12641-12646.
[26] Plaut et al. (2001) *Vaccine* 19:S148-S152.
[27] http://www.genome.ou.edu/gono.html
[28] http://www.genome.ou.edu/gono.gb gives the GenBank entry AE004969 (2153894 bp)
[29] WO99/55873
[30] WO03/010194.
[31] Kanyshkova et al. (2003) *European Journal of Biochemistry* 270:3353-
[32] Hendrixson et al. (2003) *Mol Microbiol* 47:607-617.
[33] WO03/009869.
[34] WO01/30390.
[35] Almeida & Alpar (1996) *J. Drug Targeting* 3:455-467.
[36] Agarwal & Mishra (1999) *Indian J Exp Biol* 37:6-16.
[37] Paoletti et al. (2001) *Vaccine* 19:2118-2126.
[38] WO00/56365.
[39] Gennaro (2000) *Remington: The Science and Practice of Pharmacy.* 20th edition, ISBN: 0683306472.
[40] *Vaccine Design . . .* (1995) eds. Powell & Newman. ISBN: 030644867X. Plenum.
[41] WO00/23105.
[42] WO90/14837.
[43] U.S. Pat. No. 5,057,540.
[44] WO96/33739.
[45] EP-A-0109942.
[46] WO96/11711.
[47] WO00/07621.
[48] Barr et al. (1998) *Advanced Drug Delivery Reviews* 32:247-271.
[49] Sjolander et al. (1998) *Advanced Drug Delivery Reviews* 32:321-338.
[50] Niikura et al. (2002) *Virology* 293:273-280.
[51] Lenz et al. (2001) *J Immunol* 166:5346-5355.
[52] Pinto et al. (2003) *J Infect Dis* 188:327-338.
[53] Gerber et al. (2001) *Virol* 75:4752-4760.
[54] WO03/024480

[55] WO03/024481
[56] Gluck et al. (2002) *Vaccine* 20:B10-B16.
[57] EP-A-0689454.
[58] Johnson et al. (1999) *Bioorg Med Chem Lett* 9:2273-2278.
[59] Evans et al. (2003) *Expert Rev Vaccines* 2:219-229.
[60] Meraldi et al. (2003) *Vaccine* 21:2485-2491.
[61] Pajak et al. (2003) *Vaccine* 21:836-842.
[62] Kandimalla et al. (2003) *Nucleic Acids Research* 31:2393-2400.
[63] WO02/26757.
[64] WO99/62923.
[65] Krieg (2003) *Nature Medicine* 9:831-835.
[66] McCluskie et al. (2002) *FEMS Immunology and Medical Microbiology* 32:179-185.
[67] WO98/40100.
[68] U.S. Pat. No. 6,207,646.
[69] U.S. Pat. No. 6,239,116.
[70] U.S. Pat. No. 6,429,199.
[71] Kandimalla et al. (2003) *Biochemical Society Transactions* 31 (part 3):654-658.
[72] Blackwell et al. (2003) *J Immunol* 170:4061-4068.
[73] Krieg (2002) *Trends Immunol* 23:64-65.
[74] WO01/95935.
[75] Kandimalla et al. (2003) *BBRC* 306:948-953.
[76] Bhagat et al. (2003) *BBRC* 300:853-861.
[77] WO03/035836.
[78] WO95/17211.
[79] WO98/42375.
[80] Beignon et al. (2002) *Infect Immun* 70:3012-3019.
[81] Pizza et al. (2001) *Vaccine* 19:2534-2541.
[82] Pizza et al. (2000) *Int J Med Microbiol* 290:455-461.
[83] Scharton-Kersten et al. (2000) *Infect Immun* 68:5306-5313.
[84] Ryan et al. (1999) *Infect Immun* 67:6270-6280.
[85] Partidos et al. (1999) *Immunol Lett* 67:209-216.
[86] Peppoloni et al. (2003) *Expert Rev Vaccines* 2:285-293.
[87] Pine et al. (2002) *J Control Release* 85:263-270.
[88] Domenighini et al. (1995) *Mol Microbial* 15:1165-1167.
[89] WO99/40936.
[90] WO99/44636.
[91] Singh et al. (2001) *J Cont Release* 70:267-276.
[92] WO99/27960.
[93] U.S. Pat. No. 6,090,406
[94] U.S. Pat. No. 5,916,588
[95] EP-A-0626169.
[96] WO99/52549.
[97] WO01/21207.
[98] WO01/21152.
[99] Andrianov et al. (1998) *Biomaterials* 19:109-115.
[100] Payne et al. (1998) *Adv Drug Delivery Review* 31:185-196.
[101] Stanley (2002) *Clin Exp Dermatol* 27:571-577.
[102] Jones (2003) *Curr Opin Investig Drugs* 4:214-218.
[103] WO99/11241.
[104] WO94/00153.
[105] WO98/57659.
[106] European patent applications 0835318, 0735898 and 0761231.
[107] WO96/37222; U.S. Pat. No. 6,333,036.
[108] Costantino et al. (1992) *Vaccine* 10:691-698.
[109] WO03/007985.
[110] Watson (2000) *Pediatr Infect Dis J* 19:331-332.
[111] Rubin (2000) *Pediatr Clin North Am* 47:269-285, v.
[112] Jedrzejas (2001) *Microbiol Mol Biol Rev* 65:187-207.
[113] Bell (2000) *Pediatr Infect Dis J* 19:1187-1188.
[114] Iwarson (1995) *APMIS* 103:321-326.
[115] Gerlich et al. (1990) *Vaccine* 8 Suppl:S63-68 & 79-80.
[116] *Vaccines* (1988) eds. Plotkin & Mortimer. ISBN 0-7216-1946-0.
[117] Del Guidice et al. (1998) *Molecular Aspects of Medicine* 19:1-70.
[118] Gustafsson et al. (1996) *N. Engl. J. Med.* 334:349-355.
[119] Rappuoli et al. (1991) *TIBTECH* 9:232-238.
[120] WO01/52885.
[121] Fukasawa et al. (1999) *Vaccine* 17:2951-2958.
[122] Rosenqvist et al. (1998) *Dev. Biol. Stand.* 92:323-333.
[123] Sutter et al. (2000) *Pediatr Clin North Am* 47:287-308.
[124] Zimmerman & Spann (1999) *Am Fam Physician* 59:113-118, 125-126.
[125] Anonymous (January 2002) *Research Disclosure*, 453077.
[126] Anderson (1983) *Infect Immun* 39(1):233-238.
[127] Anderson et al. (1985) *J Clin Invest* 76(1):52-59.
[128] EP-A-0372501.
[129] EP-A-0378881.
[130] EP-A-0427347.
[131] WO93/17712
[132] WO94/03208.
[133] WO98/58668.
[134] EP-A-0471177.
[135] WO91/01146
[136] Falugi et al. (2001) *Eur J Immunol* 31:3816-3824.
[137] EP-A-0594610.
[138] WO00/56360.
[139] WO02/091998.
[140] WO01/72337
[141] WO00/61761.
[142] Lees et al. (1996) *Vaccine* 14:190-198.
[143] WO95/08348.
[144] U.S. Pat. No. 4,882,317
[145] U.S. Pat. No. 4,695,624
[146] Porro et al. (1985) *Mol Immunol* 22:907-919.
[147] EP-A-0208375
[148] WO00/10599
[149] Gever et al. Med. Microbiol. Immunol, 165:171-288 (1979).
[150] U.S. Pat. No. 4,057,685.
[151] U.S. Pat. Nos. 4,673,574; 4,761,283; 4,808,700.
[152] U.S. Pat. No. 4,459,286.
[153] U.S. Pat. No. 4,965,338
[154] U.S. Pat. No. 4,663,160.
[155] U.S. Pat. No. 4,761,283
[156] U.S. Pat. No. 4,356,170
[157] Robinson & Torres (1997) *Seminars in Immunology* 9:271-283.
[158] Donnelly et al. (1997) *Annu Rev Immunol* 15:617-648.
[159] Scott-Taylor & Dalgleish (2000) *Expert Opin Investig Drugs* 9:471-480.
[160] Apostolopoulos & Plebanski (2000) *Curr Opin Mol Ther* 2:441-447.
[161] Ilan (1999) *Curr Opin Mol Ther* 1:116-120.
[162] Dubensky et al. (2000) *Mol Med* 6:723-732.
[163] Robinson & Pertmer (2000) *Adv Virus Res* 55:1-74.
[164] Donnelly et al. (2000) *Am J Respir Crit Care Med* 162(4 Pt 2):S190-193.
[165] Davis (1999) *Mt. Sinai J. Med.* 66:84-90.
[166] Charalambous & Feavers (2001) *J Med Microbiol* 50:937-939.
[167] Westerink (2001) *Int Rev Immunol* 20:251-261.
[168] Grothaus et al. (2000) *Vaccine* 18:1253-1263.
[169] *Current Protocols in Molecular Biology* (F. M. Ausubel et al., eds., 1987) Supplement 30.
[170] Smith & Waterman (1981) *Adv. Appl. Math.* 2:482-489.

The invention claimed is:

1. A method for cleaving a Neisserial '287' or 'App' polypeptide, comprising the steps of mixing the polypeptide with a lactoferrin enzyme and recovering one or more cleaved polypeptides, wherein the '287' polypeptide has 70% or more identity to SEQ ID NO: 2 and the 'App' polypeptide has 80% or more identity to SEQ ID NO: 1.

2. The method of 1, wherein the polypeptide is the '287' polypeptide, which polypeptide has 90% or more identity to SEQ ID NO: 2.

3. The method of claim 1, wherein the polypeptide is the 'App' polypeptide, which polypeptide has 90% or more identity to SEQ ID NO: 1.

4. The method of any preceding claim, wherein the lactoferrin is human lactoferrin.

* * * * *

SEQUENCE LISTING

<160> NUMBER OF SEQ ID NOS: 25

<210> SEQ ID NO 1
<211> LENGTH: 1457
<212> TYPE: PRT
<213> ORGANISM: Neisseria meningitidis

<400> SEQUENCE: 1

```
Met Lys Thr Thr Asp Lys Arg Thr Thr Glu Thr His Arg Lys Ala Pro
1               5                   10                  15

Lys Thr Gly Arg Ile Arg Phe Ser Pro Ala Tyr Leu Ala Ile Cys Leu
            20                  25                  30

Ser Phe Gly Ile Leu Pro Gln Ala Trp Ala Gly His Thr Tyr Phe Gly
        35                  40                  45

Ile Asn Tyr Gln Tyr Tyr Arg Asp Phe Ala Glu Asn Lys Gly Lys Phe
    50                  55                  60

Ala Val Gly Ala Lys Asp Ile Glu Val Tyr Asn Lys Lys Gly Glu Leu
65                  70                  75                  80

Val Gly Lys Ser Met Thr Lys Ala Pro Met Ile Asp Phe Ser Val Val
                85                  90                  95

Ser Arg Asn Gly Val Ala Ala Leu Val Gly Asp Gln Tyr Ile Val Ser
            100                 105                 110

Val Ala His Asn Gly Gly Tyr Asn Asn Val Asp Phe Gly Ala Glu Gly
        115                 120                 125

Arg Asn Pro Asp Gln His Arg Phe Thr Tyr Lys Ile Val Lys Arg Asn
    130                 135                 140

Asn Tyr Lys Ala Gly Thr Lys Gly His Pro Tyr Gly Gly Asp Tyr His
145                 150                 155                 160

Met Pro Arg Leu His Lys Phe Val Thr Asp Ala Glu Pro Val Glu Met
                165                 170                 175

Thr Ser Tyr Met Asp Gly Arg Lys Tyr Ile Asp Gln Asn Asn Tyr Pro
            180                 185                 190

Asp Arg Val Arg Ile Gly Ala Gly Arg Gln Tyr Trp Arg Ser Asp Glu
        195                 200                 205

Asp Glu Pro Asn Asn Arg Glu Ser Ser Tyr His Ile Ala Ser Ala Tyr
    210                 215                 220

Ser Trp Leu Val Gly Gly Asn Thr Phe Ala Gln Asn Gly Ser Gly Gly
225                 230                 235                 240

Gly Thr Val Asn Leu Gly Ser Glu Lys Ile Lys His Ser Pro Tyr Gly
                245                 250                 255

Phe Leu Pro Thr Gly Gly Ser Phe Gly Asp Ser Gly Ser Pro Met Phe
            260                 265                 270

Ile Tyr Asp Ala Gln Lys Gln Lys Trp Leu Ile Asn Gly Val Leu Gln
        275                 280                 285

Thr Gly Asn Pro Tyr Ile Gly Lys Ser Asn Gly Phe Gln Leu Val Arg
    290                 295                 300

Lys Asp Trp Phe Tyr Asp Glu Ile Phe Ala Gly Asp Thr His Ser Val
305                 310                 315                 320

Phe Tyr Glu Pro Arg Gln Asn Gly Lys Tyr Ser Phe Asn Asp Asp Asn
                325                 330                 335

Asn Gly Thr Gly Lys Ile Asn Ala Lys His Glu His Asn Ser Leu Pro
            340                 345                 350

Asn Arg Leu Lys Thr Arg Thr Val Gln Leu Phe Asn Val Ser Leu Ser
        355                 360                 365
```

```
Glu Thr Ala Arg Glu Pro Val Tyr His Ala Ala Gly Val Asn Ser
    370                 375                 380

Tyr Arg Pro Arg Leu Asn Asn Gly Glu Asn Ile Ser Phe Ile Asp Glu
385                 390                 395                 400

Gly Lys Gly Glu Leu Ile Leu Thr Ser Asn Ile Asn Gln Gly Ala Gly
                405                 410                 415

Gly Leu Tyr Phe Gln Gly Asp Phe Thr Val Ser Pro Glu Asn Asn Glu
            420                 425                 430

Thr Trp Gln Gly Ala Gly Val His Ile Ser Glu Asp Ser Thr Val Thr
        435                 440                 445

Trp Lys Val Asn Gly Val Ala Asn Asp Arg Leu Ser Lys Ile Gly Lys
    450                 455                 460

Gly Thr Leu His Val Gln Ala Lys Gly Glu Asn Gln Gly Ser Ile Ser
465                 470                 475                 480

Val Gly Asp Gly Thr Val Ile Leu Asp Gln Gln Ala Asp Asp Lys Gly
                485                 490                 495

Lys Lys Gln Ala Phe Ser Glu Ile Gly Leu Val Ser Gly Arg Gly Thr
            500                 505                 510

Val Gln Leu Asn Ala Asp Asn Gln Phe Asn Pro Asp Lys Leu Tyr Phe
        515                 520                 525

Gly Phe Arg Gly Gly Arg Leu Asp Leu Asn Gly His Ser Leu Ser Phe
    530                 535                 540

His Arg Ile Gln Asn Thr Asp Glu Gly Ala Met Ile Val Asn His Asn
545                 550                 555                 560

Gln Asp Lys Glu Ser Thr Val Thr Ile Thr Gly Asn Lys Asp Ile Ala
                565                 570                 575

Thr Thr Gly Asn Asn Asn Ser Leu Asp Ser Lys Lys Glu Ile Ala Tyr
            580                 585                 590

Asn Gly Trp Phe Gly Glu Lys Asp Thr Thr Lys Thr Asn Gly Arg Leu
        595                 600                 605

Asn Leu Val Tyr Gln Pro Ala Ala Glu Asp Arg Thr Leu Leu Leu Ser
    610                 615                 620

Gly Gly Thr Asn Leu Asn Gly Asn Ile Thr Gln Thr Asn Gly Lys Leu
625                 630                 635                 640

Phe Phe Ser Gly Arg Pro Thr Pro His Ala Tyr Asn His Leu Asn Asp
                645                 650                 655

His Trp Ser Gln Lys Glu Gly Ile Pro Arg Gly Glu Ile Val Trp Asp
            660                 665                 670

Asn Asp Trp Ile Asn Arg Thr Phe Lys Ala Glu Asn Phe Gln Ile Lys
        675                 680                 685

Gly Gly Gln Ala Val Val Ser Arg Asn Val Ala Lys Val Lys Gly Asp
    690                 695                 700

Trp His Leu Ser Asn His Ala Gln Ala Val Phe Gly Val Ala Pro His
705                 710                 715                 720

Gln Ser His Thr Ile Cys Thr Arg Ser Asp Trp Thr Gly Leu Thr Asn
                725                 730                 735

Cys Val Glu Lys Thr Ile Thr Asp Asp Lys Val Ile Ala Ser Leu Thr
            740                 745                 750

Lys Thr Asp Ile Ser Gly Asn Val Asp Leu Ala Asp His Ala His Leu
        755                 760                 765

Asn Leu Thr Gly Leu Ala Thr Leu Asn Gly Asn Leu Ser Ala Asn Gly
    770                 775                 780

Asp Thr Arg Tyr Thr Val Ser His Asn Ala Thr Gln Asn Gly Asn Leu
```

```
            785                 790                 795                 800
Ser Leu Val Gly Asn Ala Gln Ala Thr Phe Asn Gln Ala Thr Leu Asn
                805                 810                 815
Gly Asn Thr Ser Ala Ser Gly Asn Ala Ser Phe Asn Leu Ser Asp His
                820                 825                 830
Ala Val Gln Asn Gly Ser Leu Thr Leu Ser Gly Asn Ala Lys Ala Asn
                835                 840                 845
Val Ser His Ser Ala Leu Asn Gly Asn Val Ser Leu Ala Asp Lys Ala
                850                 855                 860
Val Phe His Phe Glu Ser Ser Arg Phe Thr Gly Gln Ile Ser Gly Gly
865                 870                 875                 880
Lys Asp Thr Ala Leu His Leu Lys Asp Ser Glu Trp Thr Leu Pro Ser
                885                 890                 895
Gly Thr Glu Leu Gly Asn Leu Asn Leu Asp Asn Ala Thr Ile Thr Leu
                900                 905                 910
Asn Ser Ala Tyr Arg His Asp Ala Ala Gly Ala Gln Thr Gly Ser Ala
                915                 920                 925
Thr Asp Ala Pro Arg Arg Ser Arg Arg Ser Arg Arg Ser Leu Leu
            930                 935                 940
Ser Val Thr Pro Pro Thr Ser Val Glu Ser Arg Phe Asn Thr Leu Thr
945                 950                 955                 960
Val Asn Gly Lys Leu Asn Gly Gln Gly Thr Phe Arg Phe Met Ser Glu
                965                 970                 975
Leu Phe Gly Tyr Arg Ser Asp Lys Leu Lys Leu Ala Glu Ser Ser Glu
                980                 985                 990
Gly Thr Tyr Thr Leu Ala Val Asn Asn Thr Gly Asn Glu Pro Ala Ser
                995                 1000                1005
Leu Glu Gln Leu Thr Val Val Glu Gly Lys Asp Asn Lys Pro Leu Ser
            1010                1015                1020
Glu Asn Leu Asn Phe Thr Leu Gln Asn Glu His Val Asp Ala Gly Ala
1025                1030                1035                1040
Trp Arg Tyr Gln Leu Ile Arg Lys Asp Gly Glu Phe Arg Leu His Asn
                1045                1050                1055
Pro Val Lys Glu Gln Glu Leu Ser Asp Lys Leu Gly Lys Ala Glu Ala
                1060                1065                1070
Lys Lys Gln Ala Glu Lys Asp Asn Ala Gln Ser Leu Asp Ala Leu Ile
            1075                1080                1085
Ala Ala Gly Arg Asp Ala Val Glu Lys Thr Gly Ser Val Ala Glu Pro
            1090                1095                1100
Ala Arg Gln Ala Gly Gly Glu Asn Val Gly Ile Met Gln Ala Glu Glu
1105                1110                1115                1120
Glu Lys Lys Arg Val Gln Ala Asp Lys Asp Thr Ala Leu Ala Lys Gln
                1125                1130                1135
Arg Glu Ala Glu Thr Arg Pro Ala Thr Thr Ala Phe Pro Arg Ala Arg
                1140                1145                1150
Arg Ala Arg Arg Asp Leu Pro Gln Leu Gln Pro Gln Pro Gln Pro Gln
            1155                1160                1165
Pro Gln Arg Asp Leu Ile Ser Arg Tyr Ala Asn Ser Gly Leu Ser Glu
            1170                1175                1180
Phe Ser Ala Thr Leu Asn Ser Val Phe Ala Val Gln Asp Glu Leu Asp
1185                1190                1195                1200
Arg Val Phe Ala Glu Asp Arg Arg Asn Ala Val Trp Thr Ser Gly Ile
                1205                1210                1215
```

```
Arg Asp Thr Lys His Tyr Arg Ser Gln Asp Phe Arg Ala Tyr Arg Gln
            1220                1225                1230

Gln Thr Asp Leu Arg Gln Ile Gly Met Gln Lys Asn Leu Gly Ser Gly
        1235                1240                1245

Arg Val Gly Ile Leu Phe Ser His Asn Arg Thr Glu Asn Thr Phe Asp
        1250                1255                1260

Asp Gly Ile Gly Asn Ser Ala Arg Leu Ala His Gly Ala Val Phe Gly
1265                1270                1275                1280

Gln Tyr Gly Ile Asp Arg Phe Tyr Ile Gly Ile Ser Ala Gly Ala Gly
            1285                1290                1295

Phe Ser Ser Gly Ser Leu Ser Asp Gly Ile Gly Gly Lys Ile Arg Arg
        1300                1305                1310

Arg Val Leu His Tyr Gly Ile Gln Ala Arg Tyr Arg Ala Gly Phe Gly
        1315                1320                1325

Gly Phe Gly Ile Glu Pro His Ile Gly Ala Thr Arg Tyr Phe Val Gln
        1330                1335                1340

Lys Ala Asp Tyr Arg Tyr Glu Asn Val Asn Ile Ala Thr Pro Gly Leu
1345                1350                1355                1360

Ala Phe Asn Arg Tyr Arg Ala Gly Ile Lys Ala Asp Tyr Ser Phe Lys
            1365                1370                1375

Pro Ala Gln His Ile Ser Ile Thr Pro Tyr Leu Ser Leu Ser Tyr Thr
        1380                1385                1390

Asp Ala Ala Ser Gly Lys Val Arg Thr Arg Val Asn Thr Ala Val Leu
        1395                1400                1405

Ala Gln Asp Phe Gly Lys Thr Arg Ser Ala Glu Trp Gly Val Asn Ala
        1410                1415                1420

Glu Ile Lys Gly Phe Thr Leu Ser Leu His Ala Ala Ala Lys Gly
1425                1430                1435                1440

Pro Gln Leu Glu Ala Gln His Ser Ala Gly Ile Lys Leu Gly Tyr Arg
            1445                1450                1455

Trp

<210> SEQ ID NO 2
<211> LENGTH: 427
<212> TYPE: PRT
<213> ORGANISM: Neisseria meningitidis

<400> SEQUENCE: 2

Met Phe Glu Arg Ser Val Ile Ala Met Ala Cys Ile Phe Ala Leu Ser
1               5                   10                  15

Ala Cys Gly Gly Gly Gly Gly Ser Pro Asp Val Lys Ser Ala Asp
                20                  25                  30

Thr Leu Ser Lys Pro Ala Ala Pro Val Val Ala Glu Lys Glu Thr Glu
        35                  40                  45

Val Lys Glu Asp Ala Pro Gln Ala Gly Ser Gln Gly Gln Gly Ala Pro
    50                  55                  60

Ser Thr Gln Gly Ser Gln Asp Met Ala Ala Val Ser Ala Glu Asn Thr
65                  70                  75                  80

Gly Asn Gly Gly Ala Ala Thr Thr Asp Lys Pro Lys Asn Glu Asp Glu
                85                  90                  95

Gly Pro Gln Asn Asp Met Pro Gln Asn Ser Ala Glu Ser Ala Asn Gln
            100                 105                 110

Thr Gly Asn Asn Gln Pro Ala Asp Ser Ser Asp Ser Ala Pro Ala Ser
        115                 120                 125

Asn Pro Ala Pro Ala Asn Gly Gly Ser Asn Phe Gly Arg Val Asp Leu
```

```
            130                 135                 140
Ala Asn Gly Val Leu Ile Asp Gly Pro Ser Gln Asn Ile Thr Leu Thr
145                 150                 155                 160

His Cys Lys Gly Asp Ser Cys Asn Gly Asp Asn Leu Leu Asp Glu Glu
                165                 170                 175

Ala Pro Ser Lys Ser Glu Phe Glu Asn Leu Asn Glu Ser Glu Arg Ile
            180                 185                 190

Glu Lys Tyr Lys Lys Asp Gly Lys Ser Asp Lys Phe Thr Asn Leu Val
                195                 200                 205

Ala Thr Ala Val Gln Ala Asn Gly Thr Asn Lys Tyr Val Ile Ile Tyr
210                 215                 220

Lys Asp Lys Ser Ala Ser Ser Ser Ala Arg Phe Arg Arg Ser Ala
225                 230                 235                 240

Arg Ser Arg Arg Ser Leu Pro Ala Glu Met Pro Leu Ile Pro Val Asn
                245                 250                 255

Gln Ala Asp Thr Leu Ile Val Asp Gly Glu Ala Val Ser Leu Thr Gly
                260                 265                 270

His Ser Gly Asn Ile Phe Ala Pro Glu Gly Asn Tyr Arg Tyr Leu Thr
                275                 280                 285

Tyr Gly Ala Glu Lys Leu Pro Gly Gly Ser Tyr Ala Leu Arg Val Gln
290                 295                 300

Gly Glu Pro Ala Lys Gly Glu Met Leu Ala Gly Thr Ala Val Tyr Asn
305                 310                 315                 320

Gly Glu Val Leu His Phe His Thr Glu Asn Gly Arg Pro Tyr Pro Thr
                325                 330                 335

Arg Gly Arg Phe Ala Ala Lys Val Asp Phe Gly Ser Lys Ser Val Asp
                340                 345                 350

Gly Ile Ile Asp Ser Gly Asp Asp Leu His Met Gly Thr Gln Lys Phe
                355                 360                 365

Lys Ala Ala Ile Asp Gly Asn Gly Phe Lys Gly Thr Trp Thr Glu Asn
            370                 375                 380

Gly Gly Gly Asp Val Ser Gly Arg Phe Tyr Gly Pro Ala Gly Glu Glu
385                 390                 395                 400

Val Ala Gly Lys Tyr Ser Tyr Arg Pro Thr Asp Ala Glu Lys Gly Gly
                405                 410                 415

Phe Gly Val Phe Ala Gly Lys Lys Glu Gln Asp
                420                 425

<210> SEQ ID NO 3
<211> LENGTH: 364
<212> TYPE: PRT
<213> ORGANISM: Neisseria meningitidis

<400> SEQUENCE: 3

Met Ser Met Lys His Phe Pro Ser Lys Val Leu Thr Thr Ala Ile Leu
1               5                   10                  15

Ala Thr Phe Cys Ser Gly Ala Leu Ala Ala Thr Ser Asp Asp Asp Val
                20                  25                  30

Lys Lys Ala Ala Thr Val Ala Ile Val Ala Ala Tyr Asn Asn Gly Gln
            35                  40                  45

Glu Ile Asn Gly Phe Lys Ala Gly Glu Thr Ile Tyr Asp Ile Gly Glu
        50                  55                  60

Asp Gly Thr Ile Thr Gln Lys Asp Ala Thr Ala Ala Asp Val Glu Ala
65                  70                  75                  80

Asp Asp Phe Lys Gly Leu Gly Leu Lys Lys Val Val Thr Asn Leu Thr
```

```
                        85                  90                  95
Lys Thr Val Asn Glu Asn Lys Gln Asn Val Asp Ala Lys Val Lys Ala
                100                 105                 110

Ala Glu Ser Glu Ile Glu Lys Leu Thr Thr Lys Leu Ala Asp Thr Asp
            115                 120                 125

Ala Ala Leu Ala Asp Thr Asp Ala Ala Leu Asp Glu Thr Thr Asn Ala
        130                 135                 140

Leu Asn Lys Leu Gly Glu Asn Ile Thr Thr Phe Ala Glu Glu Thr Lys
145                 150                 155                 160

Thr Asn Ile Val Lys Ile Asp Glu Lys Leu Glu Ala Val Ala Asp Thr
                165                 170                 175

Val Asp Lys His Ala Glu Ala Phe Asn Asp Ile Ala Asp Ser Leu Asp
            180                 185                 190

Glu Thr Asn Thr Lys Ala Asp Glu Ala Val Lys Thr Ala Asn Glu Ala
        195                 200                 205

Lys Gln Thr Ala Glu Glu Thr Lys Gln Asn Val Asp Ala Lys Val Lys
    210                 215                 220

Ala Ala Glu Thr Ala Ala Gly Lys Ala Glu Ala Ala Gly Thr Ala
225                 230                 235                 240

Asn Thr Ala Ala Asp Lys Ala Glu Ala Val Ala Lys Val Thr Asp
                245                 250                 255

Ile Lys Ala Asp Ile Ala Thr Asn Lys Ala Asp Ile Ala Lys Asn Ser
            260                 265                 270

Ala Arg Ile Asp Ser Leu Asp Lys Asn Val Ala Asn Leu Arg Lys Glu
        275                 280                 285

Thr Arg Gln Gly Leu Ala Glu Gln Ala Ala Leu Ser Gly Leu Phe Gln
    290                 295                 300

Pro Tyr Asn Val Gly Arg Phe Asn Val Thr Ala Ala Val Gly Gly Tyr
305                 310                 315                 320

Lys Ser Glu Ser Ala Val Ala Ile Gly Thr Gly Phe Arg Phe Thr Glu
                325                 330                 335

Asn Phe Ala Ala Lys Ala Gly Val Ala Val Gly Thr Ser Ser Gly Ser
            340                 345                 350

Ser Ala Ala Tyr His Val Gly Val Asn Tyr Glu Trp
        355                 360

<210> SEQ ID NO 4
<211> LENGTH: 202
<212> TYPE: PRT
<213> ORGANISM: Neisseria meningitidis

<400> SEQUENCE: 4

Met Lys Pro Lys Pro His Thr Val Arg Thr Leu Ile Ala Ala Ile Phe
1               5                   10                  15

Ser Leu Ala Leu Ser Gly Cys Val Ser Ala Val Ile Gly Ser Ala Ala
            20                  25                  30

Val Gly Ala Lys Ser Ala Val Asp Arg Arg Thr Thr Gly Ala Gln Thr
        35                  40                  45

Asp Asp Asn Val Met Ala Leu Arg Ile Glu Thr Thr Ala Arg Ser Tyr
    50                  55                  60

Leu Arg Gln Asn Asn Gln Thr Lys Gly Tyr Thr Pro Gln Ile Ser Val
65                  70                  75                  80

Val Gly Tyr Asn Arg His Leu Leu Leu Gly Gln Val Ala Thr Glu
                85                  90                  95

Gly Glu Lys Gln Phe Val Gly Gln Ile Ala Arg Ser Glu Gln Ala Ala
```

```
                         100                 105                  110
Glu Gly Val Tyr Asn Tyr Ile Thr Val Ala Ser Leu Pro Arg Thr Ala
            115                 120                 125

Gly Asp Ile Ala Gly Asp Thr Trp Asn Thr Ser Lys Val Arg Ala Thr
    130                 135                 140

Leu Leu Gly Ile Ser Pro Ala Thr Gln Ala Arg Val Lys Ile Val Thr
145                 150                 155                 160

Tyr Gly Asn Val Thr Tyr Val Met Gly Ile Leu Thr Pro Glu Glu Gln
                165                 170                 175

Ala Gln Ile Thr Gln Lys Val Ser Thr Thr Val Gly Val Gln Lys Val
            180                 185                 190

Ile Thr Leu Tyr Gln Asn Tyr Val Gln Arg
        195                 200

<210> SEQ ID NO 5
<211> LENGTH: 187
<212> TYPE: PRT
<213> ORGANISM: Neisseria meningitidis

<400> SEQUENCE: 5

Met Lys Lys Ile Ile Phe Ala Ala Leu Ala Ala Ala Ile Ser Thr
1               5                   10                  15

Ala Ser Ala Ala Thr Tyr Lys Val Asp Glu Tyr His Ala Asn Ala Arg
            20                  25                  30

Phe Ala Ile Asp His Phe Asn Thr Ser Thr Asn Val Gly Gly Phe Tyr
        35                  40                  45

Gly Leu Thr Gly Ser Val Glu Phe Asp Gln Ala Lys Arg Asp Gly Lys
    50                  55                  60

Ile Asp Ile Thr Ile Pro Ile Ala Asn Leu Gln Ser Gly Ser Gln His
65                  70                  75                  80

Phe Thr Asp His Leu Lys Ser Ala Asp Ile Phe Asp Ala Ala Gln Tyr
                85                  90                  95

Pro Asp Ile Arg Phe Val Ser Thr Lys Phe Asn Phe Asn Gly Lys Lys
            100                 105                 110

Leu Val Ser Val Asp Gly Asn Leu Thr Met His Gly Lys Thr Ala Pro
        115                 120                 125

Val Lys Leu Lys Ala Glu Lys Phe Asn Cys Tyr Gln Ser Pro Met Glu
    130                 135                 140

Lys Thr Glu Val Cys Gly Gly Asp Phe Ser Thr Thr Ile Asp Arg Thr
145                 150                 155                 160

Lys Trp Gly Met Asp Tyr Leu Val Asn Val Gly Met Thr Lys Ser Val
                165                 170                 175

Arg Ile Asp Ile Gln Ile Glu Ala Ala Lys Gln
            180                 185

<210> SEQ ID NO 6
<211> LENGTH: 145
<212> TYPE: PRT
<213> ORGANISM: Neisseria meningitidis

<400> SEQUENCE: 6

Met Gly Asn Phe Leu Tyr Arg Gly Ile Ser Cys Gln Gln Asp Glu Gln
1               5                   10                  15

Asn Asn Gly Gln Leu Lys Pro Lys Gly Asn Lys Ala Glu Val Ala Ile
            20                  25                  30

Arg Tyr Asp Gly Lys Phe Lys Tyr Asp Gly Lys Ala Thr His Gly Pro
        35                  40                  45
```

```
Ser Val Lys Asn Ala Val Tyr Ala His Gln Ile Glu Thr Gly Leu Tyr
     50                  55                  60

Asp Gly Cys Tyr Ile Ser Thr Thr Asp Lys Glu Ile Ala Lys Lys
65                  70                  75                  80

Phe Ala Thr Ser Ser Gly Ile Glu Asn Gly Tyr Ile Tyr Val Leu Asn
                 85                  90                  95

Arg Asp Leu Phe Gly Gln Tyr Ser Ile Phe Glu Tyr Glu Val Glu His
                100                 105                 110

Pro Glu Asn Pro Asn Glu Lys Glu Val Thr Ile Arg Ala Glu Asp Cys
            115                 120                 125

Gly Cys Ile Pro Glu Glu Val Ile Ile Ala Lys Glu Leu Ile Glu Ile
            130                 135                 140

Asn
145

<210> SEQ ID NO 7
<211> LENGTH: 10
<212> TYPE: PRT
<213> ORGANISM: Neisseria meningitidis

<400> SEQUENCE: 7

Ser Leu Pro Ala Glu Met Pro Leu Ile Pro
1               5                   10

<210> SEQ ID NO 8
<211> LENGTH: 173
<212> TYPE: PRT
<213> ORGANISM: Neisseria meningitidis

<400> SEQUENCE: 8

Val Asn Gln Ala Asp Thr Leu Ile Val Asp Gly Glu Ala Val Ser Leu
1               5                   10                  15

Thr Gly His Ser Gly Asn Ile Phe Ala Pro Gly Asn Tyr Arg Tyr
                 20                  25                  30

Leu Thr Tyr Gly Ala Glu Lys Leu Pro Gly Gly Ser Tyr Ala Leu Arg
                 35                  40                  45

Val Gln Gly Glu Pro Ala Lys Gly Glu Met Leu Ala Gly Thr Ala Val
     50                  55                  60

Tyr Asn Gly Glu Val Leu His Phe His Thr Glu Asn Gly Arg Pro Tyr
65                  70                  75                  80

Pro Thr Arg Gly Arg Phe Ala Ala Lys Val Asp Phe Gly Ser Lys Ser
                 85                  90                  95

Val Asp Gly Ile Ile Asp Ser Gly Asp Asp Leu His Met Gly Thr Gln
                100                 105                 110

Lys Phe Lys Ala Ala Ile Asp Gly Asn Gly Phe Lys Gly Thr Trp Thr
            115                 120                 125

Glu Asn Gly Gly Gly Asp Val Ser Gly Arg Phe Tyr Gly Pro Ala Gly
            130                 135                 140

Glu Glu Val Ala Gly Lys Tyr Ser Tyr Arg Pro Thr Asp Ala Glu Lys
145                 150                 155                 160

Gly Gly Phe Gly Val Phe Ala Gly Lys Lys Glu Gln Asp
                165                 170

<210> SEQ ID NO 9
<211> LENGTH: 243
<212> TYPE: PRT
<213> ORGANISM: Neisseria meningitidis
```

-continued

```
<400> SEQUENCE: 9

Met Phe Glu Arg Ser Val Ile Ala Met Ala Cys Ile Phe Ala Leu Ser
1               5                   10                  15

Ala Cys Gly Gly Gly Gly Gly Ser Pro Asp Val Lys Ser Ala Asp
            20                  25                  30

Thr Leu Ser Lys Pro Ala Ala Pro Val Val Ala Glu Lys Glu Thr Glu
            35                  40                  45

Val Lys Glu Asp Ala Pro Gln Ala Gly Ser Gln Gly Gln Gly Ala Pro
    50                  55                  60

Ser Thr Gln Gly Ser Gln Asp Met Ala Ala Val Ser Ala Glu Asn Thr
65                  70                  75                  80

Gly Asn Gly Gly Ala Ala Thr Thr Asp Lys Pro Lys Asn Glu Asp Glu
                85                  90                  95

Gly Pro Gln Asn Asp Met Pro Gln Asn Ser Ala Glu Ser Ala Asn Gln
            100                 105                 110

Thr Gly Asn Asn Gln Pro Ala Asp Ser Ser Asp Ser Ala Pro Ala Ser
            115                 120                 125

Asn Pro Ala Pro Ala Asn Gly Gly Ser Asn Phe Gly Arg Val Asp Leu
    130                 135                 140

Ala Asn Gly Val Leu Ile Asp Gly Pro Ser Gln Asn Ile Thr Leu Thr
145                 150                 155                 160

His Cys Lys Gly Asp Ser Cys Asn Gly Asp Asn Leu Leu Asp Glu Glu
                165                 170                 175

Ala Pro Ser Lys Ser Glu Phe Glu Asn Leu Asn Glu Ser Glu Arg Ile
            180                 185                 190

Glu Lys Tyr Lys Lys Asp Gly Lys Ser Asp Lys Phe Thr Asn Leu Val
        195                 200                 205

Ala Thr Ala Val Gln Ala Asn Gly Thr Asn Lys Tyr Val Ile Ile Tyr
    210                 215                 220

Lys Asp Lys Ser Ala Ser Ser Ser Ala Arg Phe Arg Arg Ser Ala
225                 230                 235                 240

Arg Ser Arg

<210> SEQ ID NO 10
<211> LENGTH: 219
<212> TYPE: PRT
<213> ORGANISM: Neisseria meningitidis

<400> SEQUENCE: 10

Ser Pro Asp Val Lys Ser Ala Asp Thr Leu Ser Lys Pro Ala Ala Pro
1               5                   10                  15

Val Val Ala Glu Lys Glu Thr Glu Val Lys Glu Asp Ala Pro Gln Ala
            20                  25                  30

Gly Ser Gln Gly Gln Gly Ala Pro Ser Thr Gln Gly Ser Gln Asp Met
        35                  40                  45

Ala Ala Val Ser Ala Glu Asn Thr Gly Asn Gly Gly Ala Ala Thr Thr
    50                  55                  60

Asp Lys Pro Lys Asn Glu Asp Glu Gly Pro Gln Asn Asp Met Pro Gln
65                  70                  75                  80

Asn Ser Ala Glu Ser Ala Asn Gln Thr Gly Asn Asn Gln Pro Ala Asp
                85                  90                  95

Ser Ser Asp Ser Ala Pro Ala Ser Asn Pro Ala Pro Ala Asn Gly Gly
            100                 105                 110

Ser Asn Phe Gly Arg Val Asp Leu Ala Asn Gly Val Leu Ile Asp Gly
        115                 120                 125
```

```
Pro Ser Gln Asn Ile Thr Leu Thr His Cys Lys Gly Asp Ser Cys Asn
    130                 135                 140

Gly Asp Asn Leu Leu Asp Glu Glu Ala Pro Ser Lys Ser Glu Phe Glu
145                 150                 155                 160

Asn Leu Asn Glu Ser Glu Arg Ile Glu Lys Tyr Lys Lys Asp Gly Lys
                165                 170                 175

Ser Asp Lys Phe Thr Asn Leu Val Ala Thr Ala Val Gln Ala Asn Gly
            180                 185                 190

Thr Asn Lys Tyr Val Ile Ile Tyr Lys Asp Lys Ser Ala Ser Ser Ser
        195                 200                 205

Ser Ala Arg Phe Arg Arg Ser Ala Arg Ser Arg
    210                 215

<210> SEQ ID NO 11
<211> LENGTH: 725
<212> TYPE: PRT
<213> ORGANISM: Neisseria meningitidis

<400> SEQUENCE: 11

Met Thr Arg Phe Lys Tyr Ser Leu Leu Phe Ala Ala Leu Leu Pro Val
1               5                   10                  15

Tyr Ala Gln Ala Asp Val Ser Val Ser Asp Pro Lys Pro Gln Glu
            20                  25                  30

Ser Thr Glu Leu Pro Thr Ile Thr Val Thr Ala Asp Arg Thr Ala Ser
        35                  40                  45

Ser Asn Asp Gly Tyr Thr Val Ser Gly Thr His Thr Pro Leu Gly Leu
    50                  55                  60

Pro Met Thr Leu Arg Glu Ile Pro Gln Ser Val Ser Val Ile Thr Ser
65                  70                  75                  80

Gln Gln Met Arg Asp Gln Asn Ile Lys Thr Leu Asp Arg Ala Leu Leu
                85                  90                  95

Gln Ala Thr Gly Thr Ser Arg Gln Ile Tyr Gly Ser Asp Arg Ala Gly
            100                 105                 110

Tyr Asn Tyr Leu Phe Ala Arg Gly Ser Arg Ile Ala Asn Tyr Gln Ile
        115                 120                 125

Asn Gly Ile Pro Val Ala Asp Ala Leu Ala Asp Thr Gly Asn Ala Asn
    130                 135                 140

Thr Ala Ala Tyr Glu Arg Val Glu Val Val Arg Gly Val Ala Gly Leu
145                 150                 155                 160

Leu Asp Gly Thr Gly Glu Pro Ser Ala Thr Val Asn Leu Val Arg Lys
                165                 170                 175

Arg Leu Thr Arg Lys Pro Leu Phe Glu Val Arg Ala Glu Ala Gly Asn
            180                 185                 190

Arg Lys His Phe Gly Leu Asp Ala Asp Val Ser Gly Ser Leu Asn Thr
        195                 200                 205

Glu Gly Thr Leu Arg Gly Arg Leu Val Ser Thr Phe Gly Arg Gly Asp
    210                 215                 220

Ser Trp Arg Arg Glu Arg Ser Arg Asp Ala Glu Leu Tyr Gly Ile
225                 230                 235                 240

Leu Glu Tyr Asp Ile Ala Pro Gln Thr Arg Val His Ala Gly Met Asp
                245                 250                 255

Tyr Gln Gln Ala Lys Glu Thr Ala Asp Ala Pro Leu Ser Tyr Ala Val
            260                 265                 270

Tyr Asp Ser Gln Gly Tyr Ala Thr Ala Phe Gly Pro Lys Asp Asn Pro
        275                 280                 285
```

```
Ala Thr Asn Trp Ala Asn Ser Arg His Arg Ala Leu Asn Leu Phe Ala
    290                 295                 300

Gly Ile Glu His Arg Phe Asn Gln Asp Trp Lys Leu Lys Ala Glu Tyr
305                 310                 315                 320

Asp Tyr Thr Arg Ser Arg Phe Arg Gln Pro Tyr Gly Val Ala Gly Val
                325                 330                 335

Leu Ser Ile Asp His Asn Thr Ala Thr Asp Leu Ile Pro Gly Tyr
            340                 345                 350

Trp His Ala Asp Pro Arg Thr His Ser Ala Ser Val Ser Leu Ile Gly
        355                 360                 365

Lys Tyr Arg Leu Phe Gly Arg Glu His Asp Leu Ile Ala Gly Ile Asn
370                 375                 380

Gly Tyr Lys Tyr Ala Ser Asn Lys Tyr Gly Glu Arg Ser Ile Ile Pro
385                 390                 395                 400

Asn Ala Ile Pro Asn Ala Tyr Glu Phe Ser Arg Thr Gly Ala Tyr Pro
                405                 410                 415

Gln Pro Ala Ser Phe Ala Gln Thr Ile Pro Gln Tyr Gly Thr Arg Arg
            420                 425                 430

Gln Ile Gly Gly Tyr Leu Ala Thr Arg Phe Arg Ala Ala Asp Asn Leu
        435                 440                 445

Ser Leu Ile Leu Gly Gly Arg Tyr Thr Arg Tyr Arg Thr Gly Ser Tyr
    450                 455                 460

Asp Ser Arg Thr Gln Gly Met Thr Tyr Val Ser Ala Asn Arg Phe Thr
465                 470                 475                 480

Pro Tyr Thr Gly Ile Val Phe Asp Leu Thr Gly Asn Leu Ser Leu Tyr
                485                 490                 495

Gly Ser Tyr Ser Ser Leu Phe Val Pro Gln Ser Gln Lys Asp Glu His
            500                 505                 510

Gly Ser Tyr Leu Lys Pro Val Thr Gly Asn Asn Leu Glu Ala Gly Ile
        515                 520                 525

Lys Gly Glu Trp Leu Glu Gly Arg Leu Asn Ala Ser Ala Val Tyr
    530                 535                 540

Arg Ala Arg Lys Asn Asn Leu Ala Thr Ala Ala Gly Arg Asp Pro Ser
545                 550                 555                 560

Gly Asn Thr Tyr Tyr Arg Ala Ala Asn Gln Ala Lys Thr His Gly Trp
                565                 570                 575

Glu Ile Glu Val Gly Gly Arg Ile Thr Pro Glu Trp Gln Ile Gln Ala
            580                 585                 590

Gly Tyr Ser Gln Ser Lys Thr Arg Asp Gln Asp Gly Ser Arg Leu Asn
        595                 600                 605

Pro Asp Ser Val Pro Glu Arg Ser Phe Lys Leu Phe Thr Ala Tyr His
610                 615                 620

Phe Ala Pro Glu Ala Pro Ser Gly Trp Thr Ile Gly Ala Gly Val Arg
625                 630                 635                 640

Trp Gln Ser Glu Thr His Thr Asp Pro Ala Thr Leu Arg Ile Pro Asn
                645                 650                 655

Pro Ala Ala Lys Ala Arg Ala Ala Asp Asn Ser Arg Gln Lys Ala Tyr
            660                 665                 670

Ala Val Ala Asp Ile Met Ala Arg Tyr Arg Phe Asn Pro Arg Ala Glu
        675                 680                 685

Leu Ser Leu Asn Val Asp Asn Leu Phe Asn Lys His Tyr Arg Thr Gln
690                 695                 700

Pro Asp Arg His Ser Tyr Gly Ala Leu Arg Thr Val Asn Ala Ala Phe
```

```
                705                 710                 715                 720
Thr Tyr Arg Phe Lys
                725

<210> SEQ ID NO 12
<211> LENGTH: 10
<212> TYPE: PRT
<213> ORGANISM: Neisseria meningitidis

<400> SEQUENCE: 12

Ser Leu Leu Ser Val Thr Pro Pro Thr Ser
1               5                   10

<210> SEQ ID NO 13
<211> LENGTH: 506
<212> TYPE: PRT
<213> ORGANISM: Neisseria meningitidis

<400> SEQUENCE: 13

Val Glu Ser Arg Phe Asn Thr Leu Thr Val Asn Gly Lys Leu Asn Gly
1               5                   10                  15

Gln Gly Thr Phe Arg Phe Met Ser Glu Leu Phe Gly Tyr Arg Ser Asp
            20                  25                  30

Lys Leu Lys Leu Ala Glu Ser Ser Glu Gly Thr Tyr Thr Leu Ala Val
        35                  40                  45

Asn Asn Thr Gly Asn Glu Pro Ala Ser Leu Glu Gln Leu Thr Val Val
    50                  55                  60

Glu Gly Lys Asp Asn Lys Pro Leu Ser Glu Asn Leu Asn Phe Thr Leu
65                  70                  75                  80

Gln Asn Glu His Val Asp Ala Gly Ala Trp Arg Tyr Gln Leu Ile Arg
                85                  90                  95

Lys Asp Gly Glu Phe Arg Leu His Asn Pro Val Lys Glu Gln Glu Leu
            100                 105                 110

Ser Asp Lys Leu Gly Lys Ala Glu Ala Lys Gln Ala Glu Lys Asp
        115                 120                 125

Asn Ala Gln Ser Leu Asp Ala Leu Ile Ala Ala Gly Arg Asp Ala Val
    130                 135                 140

Glu Lys Thr Glu Ser Val Ala Glu Pro Ala Arg Gln Ala Gly Gly Glu
145                 150                 155                 160

Asn Val Gly Ile Met Gln Ala Glu Glu Lys Lys Arg Val Gln Ala
                165                 170                 175

Asp Lys Asp Thr Ala Leu Ala Lys Gln Arg Glu Ala Glu Thr Arg Pro
            180                 185                 190

Ala Thr Thr Ala Phe Pro Arg Ala Arg Arg Ala Arg Asp Leu Pro
        195                 200                 205

Gln Leu Gln Pro Gln Pro Gln Pro Gln Pro Arg Asp Leu Ile Ser
    210                 215                 220

Arg Tyr Ala Asn Ser Gly Leu Ser Glu Phe Ser Ala Thr Leu Asn Ser
225                 230                 235                 240

Val Phe Ala Val Gln Asp Glu Leu Asp Arg Val Phe Ala Glu Asp Arg
                245                 250                 255

Arg Asn Ala Val Trp Thr Ser Gly Ile Arg Asp Thr Lys His Tyr Arg
            260                 265                 270

Ser Gln Asp Phe Arg Ala Tyr Arg Gln Gln Thr Asp Leu Arg Gln Ile
        275                 280                 285

Gly Met Gln Lys Asn Leu Gly Ser Gly Arg Val Gly Ile Leu Phe Ser
    290                 295                 300
```

```
His Asn Arg Thr Glu Asn Thr Phe Asp Asp Gly Ile Gly Asn Ser Ala
305                 310                 315                 320

Arg Leu Ala His Gly Ala Val Phe Gly Gln Tyr Gly Ile Asp Arg Phe
            325                 330                 335

Tyr Ile Gly Ile Ser Ala Gly Ala Phe Ser Ser Gly Ser Leu Ser
        340                 345                 350

Asp Gly Ile Gly Gly Lys Ile Arg Arg Val Leu His Tyr Gly Ile
        355                 360                 365

Gln Ala Arg Tyr Arg Ala Gly Phe Gly Phe Gly Ile Glu Pro His
        370                 375                 380

Ile Gly Ala Thr Arg Tyr Phe Val Gln Lys Ala Asp Tyr Arg Tyr Glu
385                 390                 395                 400

Asn Val Asn Ile Ala Thr Pro Gly Leu Ala Phe Asn Arg Tyr Arg Ala
                405                 410                 415

Gly Ile Lys Ala Asp Tyr Ser Phe Lys Pro Ala Gln His Ile Ser Ile
                420                 425                 430

Thr Pro Tyr Leu Ser Leu Ser Tyr Thr Asp Ala Ser Gly Lys Val
        435                 440                 445

Arg Thr Arg Val Asn Thr Ala Val Leu Ala Gln Asp Phe Gly Lys Thr
450                 455                 460

Arg Ser Ala Glu Trp Gly Val Asn Ala Glu Ile Lys Gly Phe Thr Leu
465                 470                 475                 480

Ser Leu His Ala Ala Ala Lys Gly Pro Gln Leu Glu Ala Gln His
            485                 490                 495

Ser Ala Gly Ile Lys Leu Gly Tyr Arg Trp
            500                 505

<210> SEQ ID NO 14
<211> LENGTH: 14
<212> TYPE: PRT
<213> ORGANISM: Neisseria meningitidis

<400> SEQUENCE: 14

Asp Leu Pro Gln Leu Gln Pro Gln Pro Gln Pro Gln
1               5                   10

<210> SEQ ID NO 15
<211> LENGTH: 287
<212> TYPE: PRT
<213> ORGANISM: Neisseria meningitidis

<400> SEQUENCE: 15

Arg Asp Leu Ile Ser Arg Tyr Ala Asn Ser Gly Leu Ser Glu Phe Ser
1               5                   10                  15

Ala Thr Leu Asn Ser Val Phe Ala Val Gln Asp Glu Leu Asp Arg Val
                20                  25                  30

Phe Ala Glu Asp Arg Arg Asn Ala Val Trp Thr Ser Gly Ile Arg Asp
            35                  40                  45

Thr Lys His Tyr Arg Ser Gln Asp Phe Arg Ala Tyr Arg Gln Gln Thr
    50                  55                  60

Asp Leu Arg Gln Ile Gly Met Gln Lys Asn Leu Gly Ser Gly Arg Val
65              70                  75                  80

Gly Ile Leu Phe Ser His Asn Arg Thr Glu Asn Thr Phe Asp Asp Gly
                85                  90                  95

Ile Gly Asn Ser Ala Arg Leu Ala His Gly Ala Val Phe Gly Gln Tyr
            100                 105                 110
```

```
Gly Ile Asp Arg Phe Tyr Ile Gly Ile Ser Ala Gly Ala Gly Phe Ser
            115                 120                 125

Ser Gly Ser Leu Ser Asp Gly Ile Gly Gly Lys Ile Arg Arg Arg Val
    130                 135                 140

Leu His Tyr Gly Ile Gln Ala Arg Tyr Arg Ala Gly Phe Gly Gly Phe
145                 150                 155                 160

Gly Ile Glu Pro His Ile Gly Ala Thr Arg Tyr Phe Val Gln Lys Ala
                165                 170                 175

Asp Tyr Arg Tyr Glu Asn Val Asn Ile Ala Thr Pro Gly Leu Ala Phe
            180                 185                 190

Asn Arg Tyr Arg Ala Gly Ile Lys Ala Asp Tyr Ser Phe Lys Pro Ala
        195                 200                 205

Gln His Ile Ser Ile Thr Pro Tyr Leu Ser Leu Ser Tyr Thr Asp Ala
    210                 215                 220

Ala Ser Gly Lys Val Arg Thr Arg Val Asn Thr Ala Val Leu Ala Gln
225                 230                 235                 240

Asp Phe Gly Lys Thr Arg Ser Ala Glu Trp Gly Val Asn Ala Glu Ile
                245                 250                 255

Lys Gly Phe Thr Leu Ser Leu His Ala Ala Ala Lys Gly Pro Gln
            260                 265                 270

Leu Glu Ala Gln His Ser Ala Gly Ile Lys Leu Gly Tyr Arg Trp
        275                 280                 285

<210> SEQ ID NO 16
<211> LENGTH: 940
<212> TYPE: PRT
<213> ORGANISM: Neisseria meningitidis

<400> SEQUENCE: 16

Met Lys Thr Thr Asp Lys Arg Thr Thr Glu Thr His Arg Lys Ala Pro
1               5                   10                  15

Lys Thr Gly Arg Ile Arg Phe Ser Pro Ala Tyr Leu Ala Ile Cys Leu
            20                  25                  30

Ser Phe Gly Ile Leu Pro Gln Ala Trp Ala Gly His Thr Tyr Phe Gly
        35                  40                  45

Ile Asn Tyr Gln Tyr Tyr Arg Asp Phe Ala Glu Asn Lys Gly Lys Phe
    50                  55                  60

Ala Val Gly Ala Lys Asp Ile Glu Val Tyr Asn Lys Lys Gly Glu Leu
65                  70                  75                  80

Val Gly Lys Ser Met Thr Lys Ala Pro Met Ile Asp Phe Ser Val Val
                85                  90                  95

Ser Arg Asn Gly Val Ala Ala Leu Val Gly Asp Gln Tyr Ile Val Ser
            100                 105                 110

Val Ala His Asn Gly Gly Tyr Asn Asn Val Asp Phe Gly Ala Glu Gly
        115                 120                 125

Arg Asn Pro Asp Gln His Arg Phe Thr Tyr Lys Ile Val Lys Arg Asn
    130                 135                 140

Asn Tyr Lys Ala Gly Thr Lys Gly His Pro Tyr Gly Gly Asp Tyr His
145                 150                 155                 160

Met Pro Arg Leu His Lys Phe Val Thr Asp Ala Glu Pro Val Glu Met
                165                 170                 175

Thr Ser Tyr Met Asp Gly Arg Lys Tyr Ile Asp Gln Asn Asn Tyr Pro
            180                 185                 190

Asp Arg Val Arg Ile Gly Ala Gly Arg Gln Tyr Trp Arg Ser Asp Glu
        195                 200                 205
```

```
Asp Glu Pro Asn Asn Arg Glu Ser Ser Tyr His Ile Ala Ser Ala Tyr
    210                 215                 220

Ser Trp Leu Val Gly Asn Thr Phe Ala Gln Asn Gly Ser Gly Gly
225                 230                 235                 240

Gly Thr Val Asn Leu Gly Ser Glu Lys Ile Lys His Ser Pro Tyr Gly
                245                 250                 255

Phe Leu Pro Thr Gly Gly Ser Phe Gly Asp Ser Gly Ser Pro Met Phe
            260                 265                 270

Ile Tyr Asp Ala Gln Lys Gln Lys Trp Leu Ile Asn Gly Val Leu Gln
        275                 280                 285

Thr Gly Asn Pro Tyr Ile Gly Lys Ser Asn Gly Phe Gln Leu Val Arg
    290                 295                 300

Lys Asp Trp Phe Tyr Asp Glu Ile Phe Ala Gly Asp Thr His Ser Val
305                 310                 315                 320

Phe Tyr Glu Pro Arg Gln Asn Gly Lys Tyr Ser Phe Asn Asp Asp Asn
                325                 330                 335

Asn Gly Thr Gly Lys Ile Asn Ala Lys His Glu His Asn Ser Leu Pro
            340                 345                 350

Asn Arg Leu Lys Thr Arg Thr Val Gln Leu Phe Asn Val Ser Leu Ser
        355                 360                 365

Glu Thr Ala Arg Glu Pro Val Tyr His Ala Ala Gly Gly Val Asn Ser
    370                 375                 380

Tyr Arg Pro Arg Leu Asn Asn Gly Glu Asn Ile Ser Phe Ile Asp Glu
385                 390                 395                 400

Gly Lys Gly Glu Leu Ile Leu Thr Ser Asn Ile Asn Gln Gly Ala Gly
                405                 410                 415

Gly Leu Tyr Phe Gln Gly Asp Phe Thr Val Ser Pro Glu Asn Asn Glu
            420                 425                 430

Thr Trp Gln Gly Ala Gly Val His Ile Ser Glu Asp Ser Thr Val Thr
        435                 440                 445

Trp Lys Val Asn Gly Val Ala Asn Asp Arg Leu Ser Lys Ile Gly Lys
    450                 455                 460

Gly Thr Leu His Val Gln Ala Lys Gly Glu Asn Gln Gly Ser Ile Ser
465                 470                 475                 480

Val Gly Asp Gly Thr Val Ile Leu Asp Gln Gln Ala Asp Asp Lys Gly
                485                 490                 495

Lys Lys Gln Ala Phe Ser Glu Ile Gly Leu Val Ser Gly Arg Gly Thr
            500                 505                 510

Val Gln Leu Asn Ala Asp Asn Gln Phe Asn Pro Asp Lys Leu Tyr Phe
        515                 520                 525

Gly Phe Arg Gly Gly Arg Leu Asp Leu Asn Gly His Ser Leu Ser Phe
    530                 535                 540

His Arg Ile Gln Asn Thr Asp Glu Gly Ala Met Ile Val Asn His Asn
545                 550                 555                 560

Gln Asp Lys Glu Ser Thr Val Thr Ile Thr Gly Asn Lys Asp Ile Ala
                565                 570                 575

Thr Thr Gly Asn Asn Asn Ser Leu Asp Ser Lys Lys Glu Ile Ala Tyr
            580                 585                 590

Asn Gly Trp Phe Gly Glu Lys Asp Thr Thr Lys Thr Asn Gly Arg Leu
        595                 600                 605

Asn Leu Val Tyr Gln Pro Ala Ala Glu Asp Arg Thr Leu Leu Leu Ser
    610                 615                 620

Gly Gly Thr Asn Leu Asn Gly Asn Ile Thr Gln Thr Asn Gly Lys Leu
625                 630                 635                 640
```

```
Phe Phe Ser Gly Arg Pro Thr Pro His Ala Tyr Asn His Leu Asn Asp
                645                 650                 655

His Trp Ser Gln Lys Glu Gly Ile Pro Arg Gly Glu Ile Val Trp Asp
            660                 665                 670

Asn Asp Trp Ile Asn Arg Thr Phe Lys Ala Glu Asn Phe Gln Ile Lys
                675                 680                 685

Gly Gly Gln Ala Val Val Ser Arg Asn Val Ala Lys Val Lys Gly Asp
690                 695                 700

Trp His Leu Ser Asn His Ala Gln Ala Val Phe Gly Val Ala Pro His
705                 710                 715                 720

Gln Ser His Thr Ile Cys Thr Arg Ser Asp Trp Thr Gly Leu Thr Asn
                725                 730                 735

Cys Val Glu Lys Thr Ile Thr Asp Asp Lys Val Ile Ala Ser Leu Thr
                740                 745                 750

Lys Thr Asp Ile Ser Gly Asn Val Asp Leu Ala Asp His Ala His Leu
            755                 760                 765

Asn Leu Thr Gly Leu Ala Thr Leu Asn Gly Asn Leu Ser Ala Asn Gly
770                 775                 780

Asp Thr Arg Tyr Thr Val Ser His Asn Ala Thr Gln Asn Gly Asn Leu
785                 790                 795                 800

Ser Leu Val Gly Asn Ala Gln Ala Thr Phe Asn Gln Ala Thr Leu Asn
                805                 810                 815

Gly Asn Thr Ser Ala Ser Gly Asn Ala Ser Phe Asn Leu Ser Asp His
            820                 825                 830

Ala Val Gln Asn Gly Ser Leu Thr Leu Ser Gly Asn Ala Lys Ala Asn
                835                 840                 845

Val Ser His Ser Ala Leu Asn Gly Asn Val Ser Leu Ala Asp Lys Ala
            850                 855                 860

Val Phe His Phe Glu Ser Ser Arg Phe Thr Gly Gln Ile Ser Gly Gly
865                 870                 875                 880

Lys Asp Thr Ala Leu His Leu Lys Asp Ser Glu Trp Thr Leu Pro Ser
                885                 890                 895

Gly Thr Glu Leu Gly Asn Leu Asn Leu Asp Asn Ala Thr Ile Thr Leu
            900                 905                 910

Asn Ser Ala Tyr Arg His Asp Ala Ala Gly Ala Gln Thr Gly Ser Ala
                915                 920                 925

Thr Asp Ala Pro Arg Arg Ser Arg Arg Ser Arg
930                 935                 940

<210> SEQ ID NO 17
<211> LENGTH: 1155
<212> TYPE: PRT
<213> ORGANISM: Neisseria meningitidis

<400> SEQUENCE: 17

Met Lys Thr Thr Asp Lys Arg Thr Thr Glu Thr His Arg Lys Ala Pro
1               5                   10                  15

Lys Thr Gly Arg Ile Arg Phe Ser Pro Ala Tyr Leu Ala Ile Cys Leu
            20                  25                  30

Ser Phe Gly Ile Leu Pro Gln Ala Trp Ala Gly His Thr Tyr Phe Gly
        35                  40                  45

Ile Asn Tyr Gln Tyr Tyr Arg Asp Phe Ala Glu Asn Lys Gly Lys Phe
    50                  55                  60

Ala Val Gly Ala Lys Asp Ile Glu Val Tyr Asn Lys Lys Gly Glu Leu
65                  70                  75                  80
```

-continued

Val Gly Lys Ser Met Thr Lys Ala Pro Met Ile Asp Phe Ser Val Val
                85                  90                  95

Ser Arg Asn Gly Val Ala Ala Leu Val Gly Asp Gln Tyr Ile Val Ser
            100                 105                 110

Val Ala His Asn Gly Gly Tyr Asn Asn Val Asp Phe Gly Ala Glu Gly
        115                 120                 125

Arg Asn Pro Asp Gln His Arg Phe Thr Tyr Lys Ile Val Lys Arg Asn
    130                 135                 140

Asn Tyr Lys Ala Gly Thr Lys Gly His Pro Tyr Gly Gly Asp Tyr His
145                 150                 155                 160

Met Pro Arg Leu His Lys Phe Val Thr Asp Ala Glu Pro Val Glu Met
                165                 170                 175

Thr Ser Tyr Met Asp Gly Arg Lys Tyr Ile Asp Gln Asn Asn Tyr Pro
            180                 185                 190

Asp Arg Val Arg Ile Gly Ala Gly Arg Gln Tyr Trp Arg Ser Asp Glu
        195                 200                 205

Asp Glu Pro Asn Asn Arg Glu Ser Ser Tyr His Ile Ala Ser Ala Tyr
    210                 215                 220

Ser Trp Leu Val Gly Asn Thr Phe Ala Gln Asn Gly Ser Gly Gly
225                 230                 235                 240

Gly Thr Val Asn Leu Gly Ser Glu Lys Ile Lys His Ser Pro Tyr Gly
                245                 250                 255

Phe Leu Pro Thr Gly Gly Ser Phe Gly Asp Ser Gly Ser Pro Met Phe
            260                 265                 270

Ile Tyr Asp Ala Gln Lys Gln Lys Trp Leu Ile Asn Gly Val Leu Gln
        275                 280                 285

Thr Gly Asn Pro Tyr Ile Gly Lys Ser Asn Gly Phe Gln Leu Val Arg
    290                 295                 300

Lys Asp Trp Phe Tyr Asp Glu Ile Phe Ala Gly Asp Thr His Ser Val
305                 310                 315                 320

Phe Tyr Glu Pro Arg Gln Asn Gly Lys Tyr Ser Phe Asn Asp Asp Asn
                325                 330                 335

Asn Gly Thr Gly Lys Ile Asn Ala Lys His Glu His Asn Ser Leu Pro
            340                 345                 350

Asn Arg Leu Lys Thr Arg Thr Val Gln Leu Phe Asn Val Ser Leu Ser
        355                 360                 365

Glu Thr Ala Arg Glu Pro Val Tyr His Ala Ala Gly Gly Val Asn Ser
    370                 375                 380

Tyr Arg Pro Arg Leu Asn Asn Gly Glu Asn Ile Ser Phe Ile Asp Glu
385                 390                 395                 400

Gly Lys Gly Glu Leu Ile Leu Thr Ser Asn Ile Asn Gln Gly Ala Gly
                405                 410                 415

Gly Leu Tyr Phe Gln Gly Asp Phe Thr Val Ser Pro Glu Asn Asn Glu
            420                 425                 430

Thr Trp Gln Gly Ala Gly Val His Ile Ser Glu Asp Ser Thr Val Thr
        435                 440                 445

Trp Lys Val Asn Gly Val Ala Asn Asp Arg Leu Ser Lys Ile Gly Lys
    450                 455                 460

Gly Thr Leu His Val Gln Ala Lys Gly Glu Asn Gln Gly Ser Ile Ser
465                 470                 475                 480

Val Gly Asp Gly Thr Val Ile Leu Asp Gln Gln Ala Asp Asp Lys Gly
                485                 490                 495

Lys Lys Gln Ala Phe Ser Glu Ile Gly Leu Val Ser Gly Arg Gly Thr

-continued

```
                500                 505                 510
Val Gln Leu Asn Ala Asp Asn Gln Phe Asn Pro Asp Lys Leu Tyr Phe
            515                 520                 525

Gly Phe Arg Gly Gly Arg Leu Asp Leu Asn Gly His Ser Leu Ser Phe
        530                 535                 540

His Arg Ile Gln Asn Thr Asp Glu Gly Ala Met Ile Val Asn His Asn
545                 550                 555                 560

Gln Asp Lys Glu Ser Thr Val Thr Ile Thr Gly Asn Lys Asp Ile Ala
                565                 570                 575

Thr Thr Gly Asn Asn Asn Ser Leu Asp Ser Lys Lys Glu Ile Ala Tyr
            580                 585                 590

Asn Gly Trp Phe Gly Glu Lys Asp Thr Thr Lys Thr Asn Gly Arg Leu
        595                 600                 605

Asn Leu Val Tyr Gln Pro Ala Ala Glu Asp Arg Thr Leu Leu Leu Ser
    610                 615                 620

Gly Gly Thr Asn Leu Asn Gly Asn Ile Thr Gln Thr Asn Gly Lys Leu
625                 630                 635                 640

Phe Phe Ser Gly Arg Pro Thr Pro His Ala Tyr Asn His Leu Asn Asp
                645                 650                 655

His Trp Ser Gln Lys Glu Gly Ile Pro Arg Gly Glu Ile Val Trp Asp
            660                 665                 670

Asn Asp Trp Ile Asn Arg Thr Phe Lys Ala Glu Asn Phe Gln Ile Lys
        675                 680                 685

Gly Gly Gln Ala Val Val Ser Arg Asn Val Ala Lys Val Lys Gly Asp
    690                 695                 700

Trp His Leu Ser Asn His Ala Gln Ala Val Phe Gly Val Ala Pro His
705                 710                 715                 720

Gln Ser His Thr Ile Cys Thr Arg Ser Asp Trp Thr Gly Leu Thr Asn
                725                 730                 735

Cys Val Glu Lys Thr Ile Thr Asp Lys Val Ile Ala Ser Leu Thr
            740                 745                 750

Lys Thr Asp Ile Ser Gly Asn Val Asp Leu Ala Asp His Ala His Leu
        755                 760                 765

Asn Leu Thr Gly Leu Ala Thr Leu Asn Gly Asn Leu Ser Ala Asn Gly
    770                 775                 780

Asp Thr Arg Tyr Thr Val Ser His Asn Ala Thr Gln Asn Gly Asn Leu
785                 790                 795                 800

Ser Leu Val Gly Asn Ala Gln Ala Thr Phe Asn Gln Ala Thr Leu Asn
                805                 810                 815

Gly Asn Thr Ser Ala Ser Gly Asn Ala Ser Phe Asn Leu Ser Asp His
            820                 825                 830

Ala Val Gln Asn Gly Ser Leu Thr Leu Ser Gly Asn Ala Lys Ala Asn
        835                 840                 845

Val Ser His Ser Ala Leu Asn Gly Asn Val Ser Leu Ala Asp Lys Ala
    850                 855                 860

Val Phe His Phe Glu Ser Ser Arg Phe Thr Gly Gln Ile Ser Gly Gly
865                 870                 875                 880

Lys Asp Thr Ala Leu His Leu Lys Asp Ser Glu Trp Thr Leu Pro Ser
                885                 890                 895

Gly Thr Glu Leu Gly Asn Leu Asn Leu Asp Asn Ala Thr Ile Thr Leu
            900                 905                 910

Asn Ser Ala Tyr Arg His Asp Ala Ala Gly Ala Gln Thr Gly Ser Ala
        915                 920                 925
```

Thr Asp Ala Pro Arg Arg Arg Ser Arg Arg Ser Leu Leu
    930             935             940

Ser Val Thr Pro Pro Thr Ser Val Glu Ser Arg Phe Asn Thr Leu Thr
945                 950             955                 960

Val Asn Gly Lys Leu Asn Gly Gln Gly Thr Phe Arg Phe Met Ser Glu
                965             970             975

Leu Phe Gly Tyr Arg Ser Asp Lys Leu Lys Leu Ala Glu Ser Ser Glu
            980             985             990

Gly Thr Tyr Thr Leu Ala Val Asn Asn Thr Gly Asn Glu Pro Ala Ser
        995             1000            1005

Leu Glu Gln Leu Thr Val Val Glu Gly Lys Asp Asn Lys Pro Leu Ser
    1010            1015            1020

Glu Asn Leu Asn Phe Thr Leu Gln Asn Glu His Val Asp Ala Gly Ala
1025            1030            1035            1040

Trp Arg Tyr Gln Leu Ile Arg Lys Asp Gly Glu Phe Arg Leu His Asn
            1045            1050            1055

Pro Val Lys Glu Gln Glu Leu Ser Asp Lys Leu Gly Lys Ala Glu Ala
            1060            1065            1070

Lys Lys Gln Ala Glu Lys Asp Asn Ala Gln Ser Leu Asp Ala Leu Ile
    1075            1080            1085

Ala Ala Gly Arg Asp Ala Val Glu Lys Thr Glu Ser Val Ala Glu Pro
    1090            1095            1100

Ala Arg Gln Ala Gly Gly Glu Asn Val Gly Ile Met Gln Ala Glu Glu
1105            1110            1115            1120

Glu Lys Lys Arg Val Gln Ala Asp Lys Asp Thr Ala Leu Ala Lys Gln
            1125            1130            1135

Arg Glu Ala Glu Thr Arg Pro Ala Thr Thr Ala Phe Pro Arg Ala Arg
            1140            1145            1150

Arg Ala Arg
    1155

<210> SEQ ID NO 18
<211> LENGTH: 10
<212> TYPE: PRT
<213> ORGANISM: Neisseria meningitidis

<400> SEQUENCE: 18

Lys Ser Ala Ser Ser Ser Ser Ala Arg Phe
1               5                   10

<210> SEQ ID NO 19
<211> LENGTH: 10
<212> TYPE: PRT
<213> ORGANISM: Neisseria meningitidis

<400> SEQUENCE: 19

Ala Gln Thr Gly Ser Ala Thr Asp Ala Pro
1               5                   10

<210> SEQ ID NO 20
<211> LENGTH: 10
<212> TYPE: PRT
<213> ORGANISM: Neisseria meningitidis

<400> SEQUENCE: 20

Glu Thr Arg Pro Ala Thr Thr Ala Phe Pro
1               5                   10

<210> SEQ ID NO 21

-continued

```
<211> LENGTH: 8
<212> TYPE: PRT
<213> ORGANISM: Neisseria meningitidis

<400> SEQUENCE: 21

Arg Arg Ser Ala Arg Ser Arg Arg
1               5

<210> SEQ ID NO 22
<211> LENGTH: 9
<212> TYPE: PRT
<213> ORGANISM: Neisseria meningitidis

<400> SEQUENCE: 22

Arg Arg Arg Ser Arg Arg Ser Arg Arg
1               5

<210> SEQ ID NO 23
<211> LENGTH: 7
<212> TYPE: PRT
<213> ORGANISM: Neisseria meningitidis

<400> SEQUENCE: 23

Arg Ala Arg Arg Ala Arg Arg
1               5

<210> SEQ ID NO 24
<211> LENGTH: 9
<212> TYPE: PRT
<213> ORGANISM: Neisseria meningitidis

<400> SEQUENCE: 24

Ser Leu Pro Ala Glu Met Pro Leu Ile
1               5

<210> SEQ ID NO 25
<211> LENGTH: 9
<212> TYPE: PRT
<213> ORGANISM: Neisseria meningitidis

<400> SEQUENCE: 25

Arg Ser Leu Pro Ala Glu Met Pro Leu
1               5
```